(12) United States Patent
Adam

(10) Patent No.: US 8,911,858 B2
(45) Date of Patent: Dec. 16, 2014

(54) MULTIFUNCTIONAL MELAMINE EPOXY RESINS, METHYLOLS AND AMINES

(71) Applicant: Empire Technology Development LLC, Wilmington, DE (US)

(72) Inventor: Georgius Abidal Adam, Edensor Park (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/879,289

(22) PCT Filed: Oct. 31, 2012

(86) PCT No.: PCT/US2012/062708
§ 371 (c)(1),
(2), (4) Date: Apr. 12, 2013

(87) PCT Pub. No.: WO2014/070155
PCT Pub. Date: May 8, 2014

(65) Prior Publication Data
US 2014/0179838 A1    Jun. 26, 2014

(51) Int. Cl.
*B32B 27/04* (2006.01)
*B32B 27/38* (2006.01)
*C08G 59/32* (2006.01)
*C08G 71/02* (2006.01)
*C07D 251/70* (2006.01)
*C08G 65/00* (2006.01)
*C08G 18/02* (2006.01)
*C08K 7/06* (2006.01)

(52) U.S. Cl.
CPC . *C08K 7/06* (2013.01); *C08G 65/00* (2013.01); *C08G 18/02* (2013.01); *C07D 251/70* (2013.01)
USPC ............................ 428/299.1; 528/68; 544/196

(58) Field of Classification Search
None
See application file for complete search history.

(56) References Cited

U.S. PATENT DOCUMENTS

| | | | |
|---|---|---|---|
| 2,980,676 A | | 4/1961 | Zuppinger et al. |
| 3,726,835 A | * | 4/1973 | Bertozzi .......................... 528/61 |
| 4,038,455 A | | 7/1977 | Wampetich |
| 4,623,701 A | | 11/1986 | Massingill |
| 4,661,568 A | | 4/1987 | Koenig et al. |
| 5,939,515 A | | 8/1999 | Guenther et al. |
| 6,004,892 A | | 12/1999 | Guenther et al. |
| 6,297,178 B1 | | 10/2001 | Berbner et al. |

FOREIGN PATENT DOCUMENTS

EP    2149572 A1 *   2/2010 ........... C07D 405/12

OTHER PUBLICATIONS

Machine translation of EP 2149572 A1, provided by the EPO website (no date).*
International Search Report and Written Opinion for PCT/US2012/062708 dated Jan. 9, 2013.
Arlon Technology Enabling Innovation, Multifunctional, High Tg Epoxy Low—Flow Prepreg, www.arlon-med.com (Printed from Internet Feb. 11, 2013).
Atta et al., Synthesis of bisphenol a novolac epoxy resins for coating applications, *J. Appl. Polym. Sci.* (Sep. 19, 2007), 107(1):347-354 (Abstract).
Auchmoody et al., Effect of Calcium Cyanamide, on Growth and Nutrition of Planted Yellow-Poplar Seedlings, Forest Service Department of Agriculture, USDA Forest Service Research Paper Ne-265 (1973), pp. 1-14.
Cech et al., The Effectiveness of Toughening Technologies on Multifunctional Epoxy Resin Systems, pp. 1-15 (Printed from Internet Feb. 11, 2013) http://www.cvc.emeraldmaterials.com/epm/cvc/micms_doc_admin.display?p_customer=FISCVC&p_name=SPI%20PAPER%20ON%20CTBN%20MODIFIED%20EPNS.PDF.
Chech, characteristics of Bis F and Phenol Novolac Epoxy Resins, *Compositional differences and their effect on Performance*, http://www.emeraldmaterials.com/epm/cvc/micms_doc_admin.display?p_customer=FISCVC&p_name=CHEMISTRY%20AND%20COMPOSITION%20OF%20EPN%20RESINS.PDF (Printed from Internet Feb. 28, 2013).
Cheng et al., Synthesis and characterization of novel multifunctional epoxy resin, *Chinese Chemical Letters* (Apr. 2007), 18(4):469-472 (Abstract).
Epoxy Resins, http://info.smithersrapra.com/downloads/chapters/Thermoset%20Resins.pdf (Printed from Internet Feb. 28, 2013 ).
Epoxy Resins, Aditya Birla Chemicals, http://www.adityabirlachemicals.com/products/epoxy_resins/epoxy_resins_overview.html (Printed from Internet Feb. 28, 2013).
Liu et al., Halogen-free flame retardant epoxy resins from hybrids of phosphorus- or silicon-containing epoxies with an amine resin, *Journal of Applied Polymer Science* (Jul. 28, 2006), 102(2):1071-1077 (Abstract).
Liu et al., Curing Behavior and Thermal Properties of Multifunctional Epoxy Resin with Methylhexahydrophthalic Anhydride, *Journal of Applied Polymer Science* (2007), 103:2041-2048.
Lubczak, Polyhydroxyalkyl derivatives and polyetherols obtained from azacyclic compounds, Part II. Reactions with Formaldehyde and Alkylene Carbonates, *Polimery* (2011), 56(6):452-460.
Melamine, http://en.wikipedia.org/wiki/Melamine (Printed from Internet Feb. 11, 2013).
Momentive.com Product Offering, http://www.momentive.com/productfamily/home.aspx?id=8846 (Printed from Internet Feb. 28, 2013).
Momentive.com, http://www.momentive.com/home.aspx (Printed from Internet Feb. 28, 2013).
Pedroso et al., Melamine/epichlorohydrin prepolymers: syntheses and characterization, *Polymer* (Jan. 19, 2005), 46:1766-1774.
Swanson et al., Investigation of network development and properties in multifunctional epoxy resins using 3,3'-diaminodiphenylsulfone, pp. 1-15, http://www.trfa.org/Documents/Entry7-Swanson.pdf (Printed from Internet Feb. 11, 2013).
World Epoxy Resin Market, Market Report, Acmite Market Intelligence (Oct. 2010).

* cited by examiner

*Primary Examiner* — Michael J Feely
(74) *Attorney, Agent, or Firm* — Pepper Hamilton LLP

(57) ABSTRACT

Multifunctional melamine epoxy resins, methylols and amines are provided. Methods of making multifunctional melamine epoxy resins, methylols and amines are also provided.

19 Claims, No Drawings

MULTIFUNCTIONAL MELAMINE EPOXY RESINS, METHYLOLS AND AMINES

CLAIM OF PRIORITY

This application is a U.S. national stage filing under 35 U.S.C. §371 of International Application No. PCT/US2012/062708 filed Oct. 31, 2012, entitled "MULTIFUNCTIONAL MELAMINE EPOXY RESINS, METHYLOLS AND AMINES," which is incorporated by reference in its entirety.

FIELD

Multi-functional epoxy resins for composite materials, methods of making, and uses thereof are provided.

BACKGROUND

Epoxy resins are used as the predominant ingredient in the fabrication of composite parts and can be utilized both as matrix resin and as crosslinking agents. The degree of functionality of the resin is critical in determining the final properties and the range of end-use applications. Accordingly, production of new resins with enhanced functionality and improved toughness will have a wide range of applications in various fields of composites, coatings, paints, and Interpenetrating Polymer Networks (IPNs). New resins must not only have the requisite properties, but also can be obtained from non-petrochemical sources and have a demonstrably lower materials life cycle cost. The majority of polyfunctional epoxies are sourced from petrochemicals such as, for example, those based on Novolac epoxy. There are others based on polyhydroxy compounds such as glycerol, and epoxy esters derived from polycarboxylic acids as alliterative multi-functional epoxy resins. Several melamine formaldehyde resins are known compounds and produced industrially such as: melamine oil, melamine hexamethylol esters.

There is still a need for improved melamine resins and for new uses and applications of the same with increased functionality. The present application fulfills these needs as well as others.

SUMMARY OF THE INVENTION

In some embodiments, compounds having the structure of Formula III:

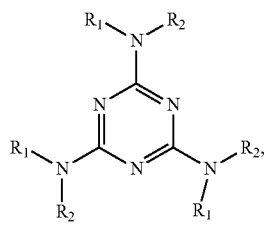

III

In some embodiments, $R_1$ and $R_2$ are each independently selected from the group consisting of:

H, —CH$_2$OH, —CH$_2$OR$_3$, —CH$_2$N(CH$_2$CH$_2$OH)$_2$,

—CH$_2$N(CH$_2$CH$_2$NH$_2$)$_2$, 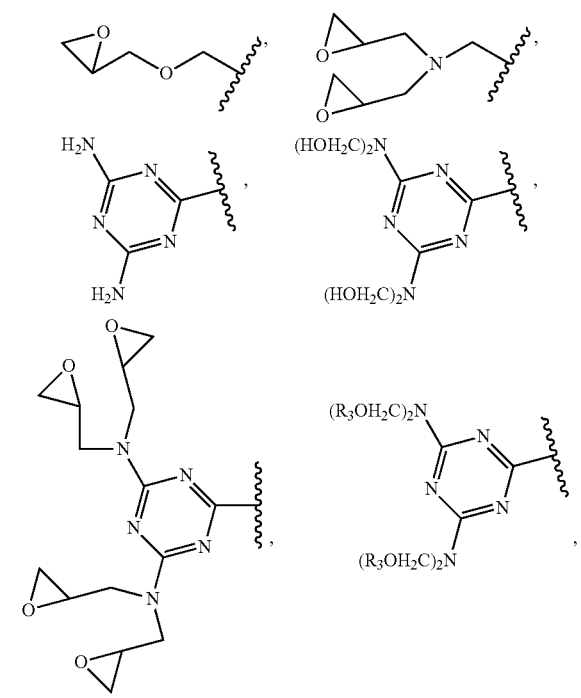

and
$R_3$ is

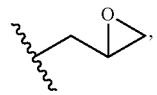 [SMILES: *CC1CO1]

provided that when $R_1$ is H, $R_2$ is not H or —CH$_2$OH are provided.

In some embodiments, the compound has the formula of:

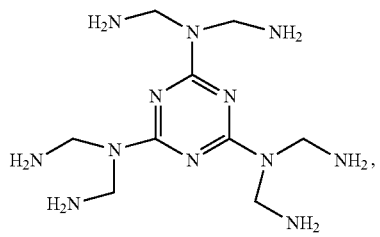

IV

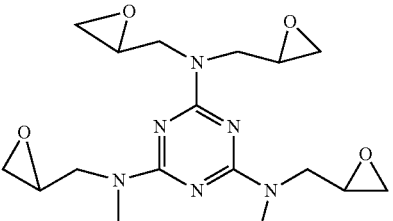

V

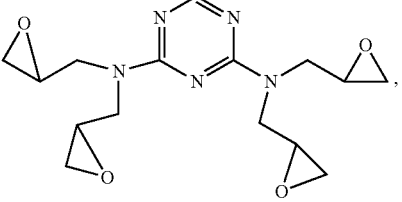

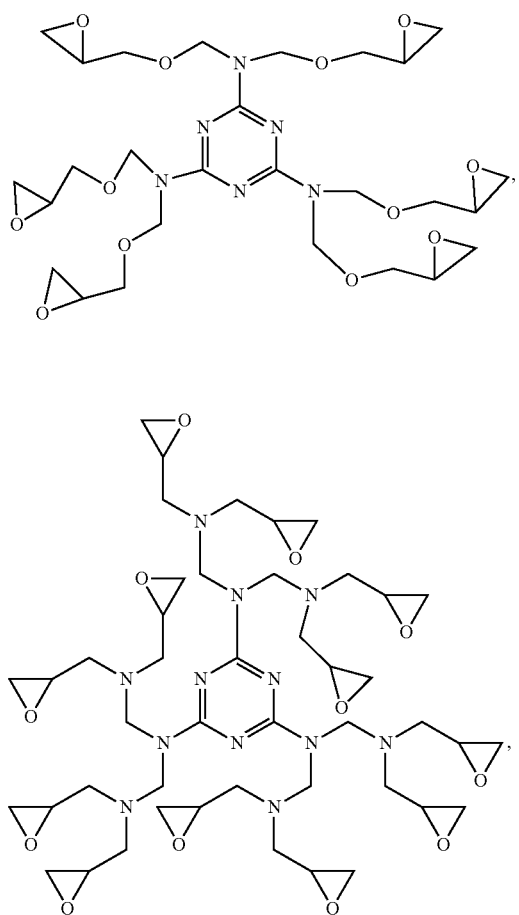
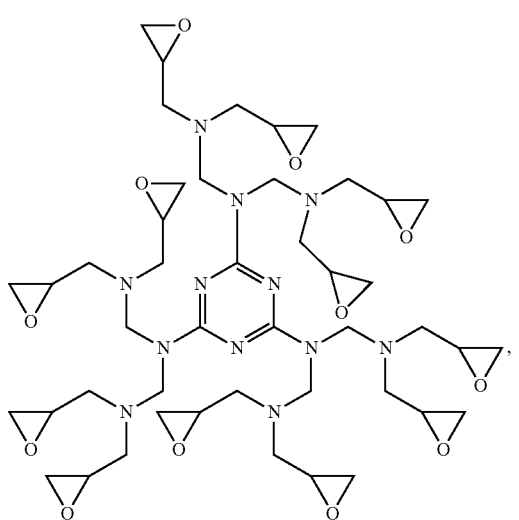
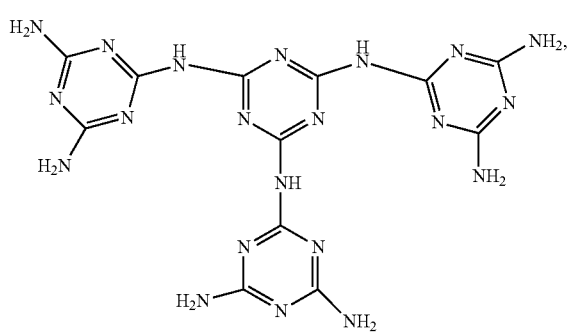
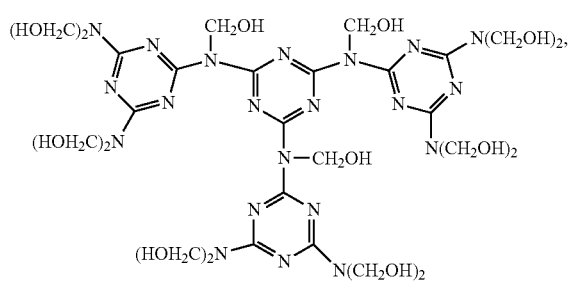
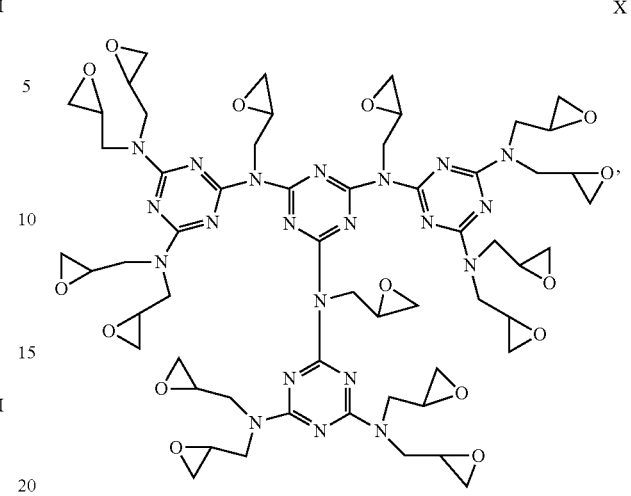
In some embodiments, compositions are provided, the compositions comprising one or more of the compounds having the formula of Formula III:
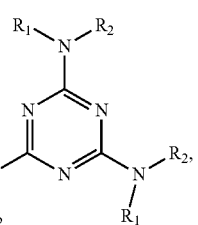
wherein $R_1$ and $R_2$ are each independently selected from the group consisting of:

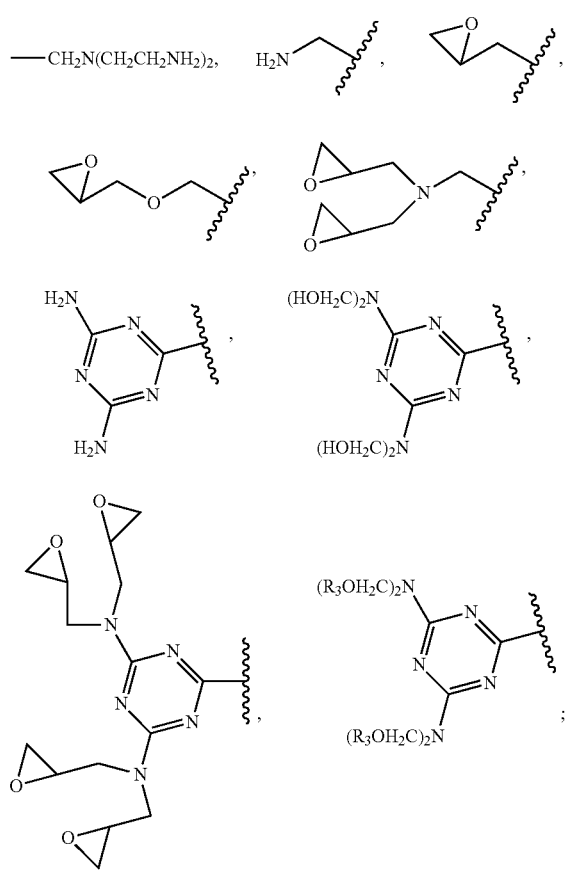

and
R₃ is

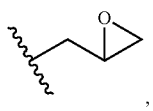 [SMILES: *CC1CO1]

provided that when R₁ is H, R₂ is not H or —CH₂OH.

In some embodiments, epoxy resins are provided, the epoxy resins comprising a compound having the structure of Formula III:

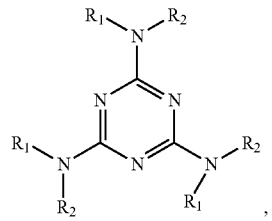

III wherein R₁ and R₂ are each independently selected from the group consisting epoxy groups of:

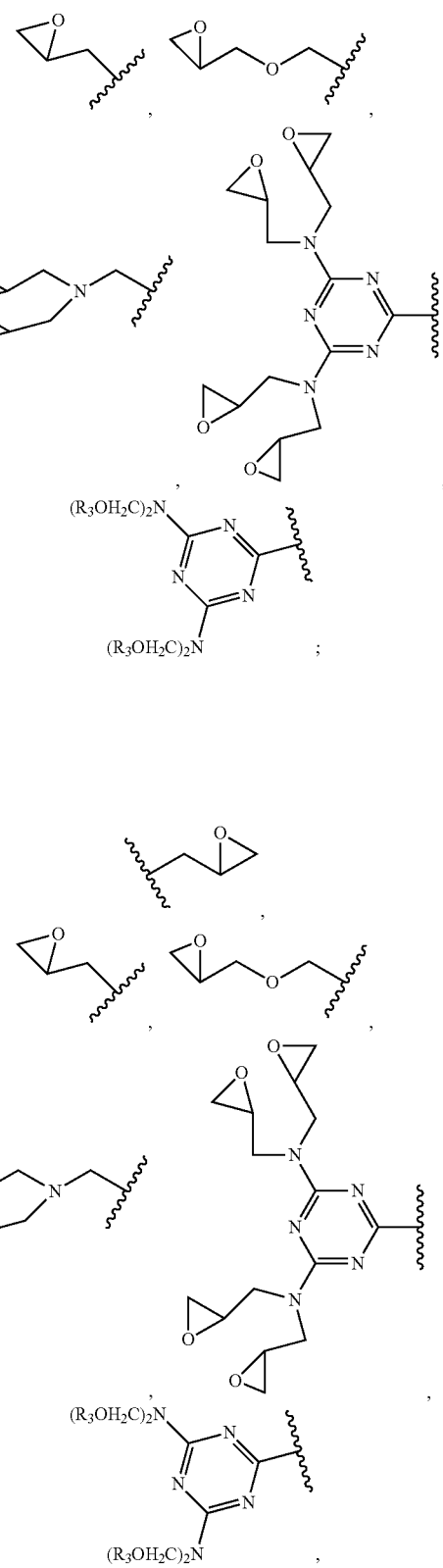

In some embodiments, carbon fiber composites are provided, the composites comprising a cured epoxy resin of an epoxy resin and amino hardeners, wherein the epoxy resin is a compound of Formula III

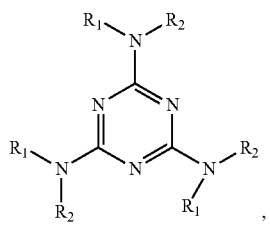
wherein $R_1$ and $R_2$ are independently selected from the group consisting of:
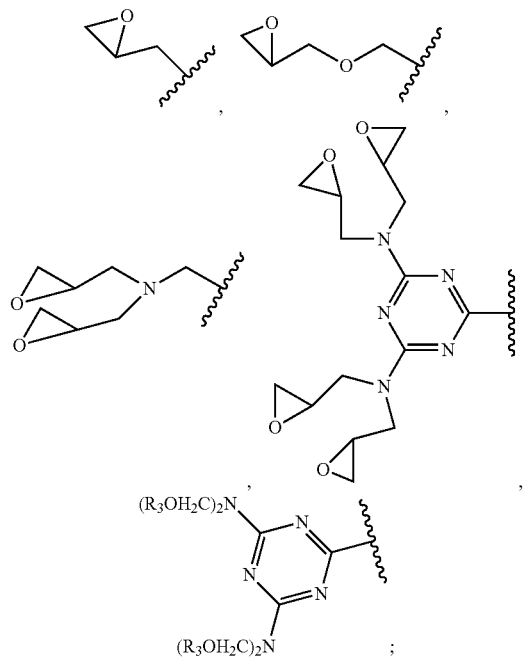
and
$R_3$ is
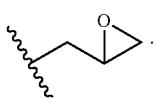 [SMILES: *CC1CO1]
In some embodiments, the composites comprises an epoxy resin having a Formula of
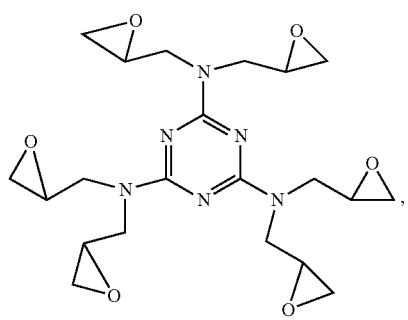
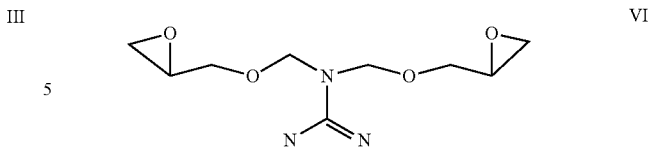
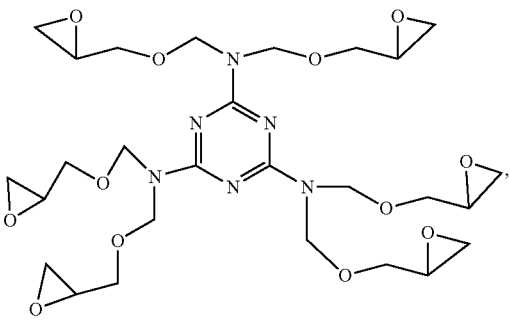
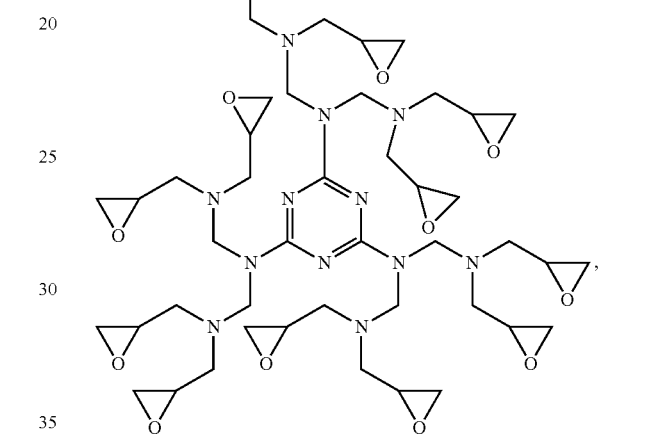
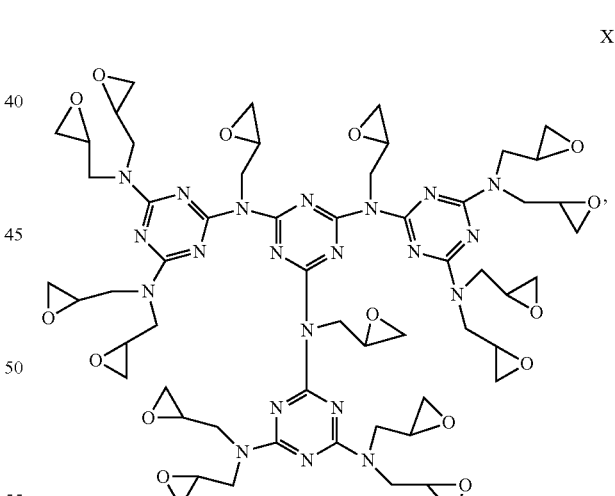
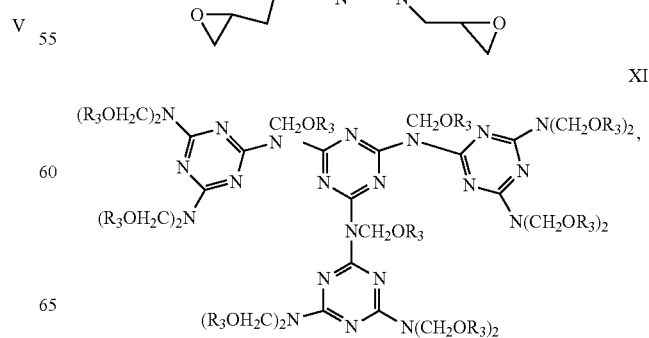

wherein $R_3$ is

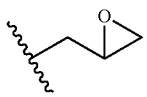

In some embodiments cross-linked isocyanate terminated polyurethanes, polyesters, or silicones, wherein the isocyanate terminated polyurethanes, polyester, or silicone are cross-linked with a compound of Formula III

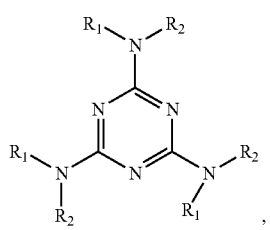
III wherein $R_1$ and $R_2$ are independently selected from the group consisting of H, $CH_2OH$ $CH_2NH_2$, and melaminyl, or are cross-linked with a compound having a formula of

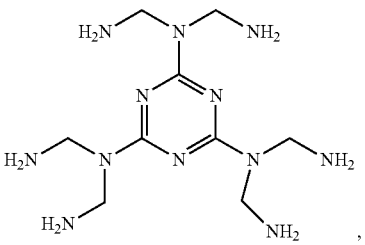
IV

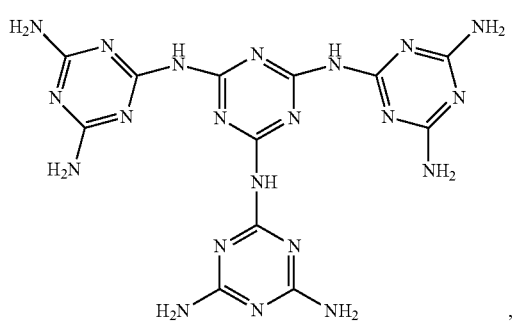
VIII

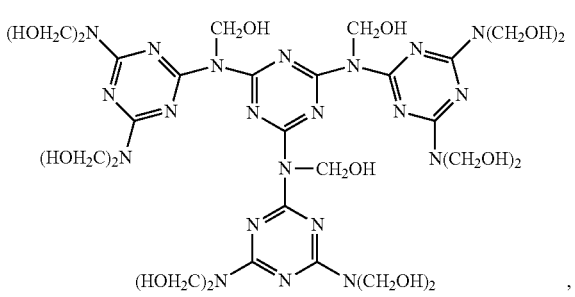
IX

XII

, or

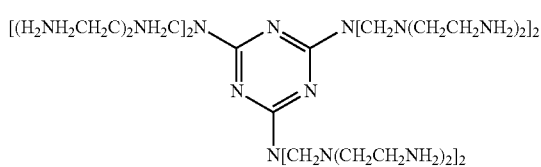
XIII are provided.

In some embodiments, composites are provided, the composites comprising one or more a cured epoxy resins of an epoxy resin of Formula III, wherein the epoxy resin is a compound of Formula III

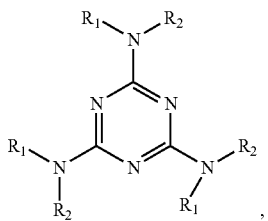
III wherein $R_1$ and $R_2$ are independently selected from the group consisting of:

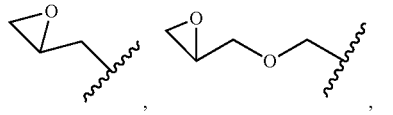

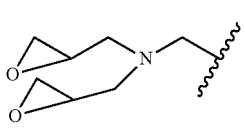

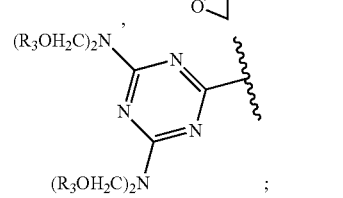

and
$R_3$ is

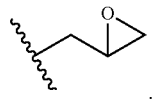 [SMILES: *CC1CO1]

In some embodiments, the epoxy resin has a Formula of

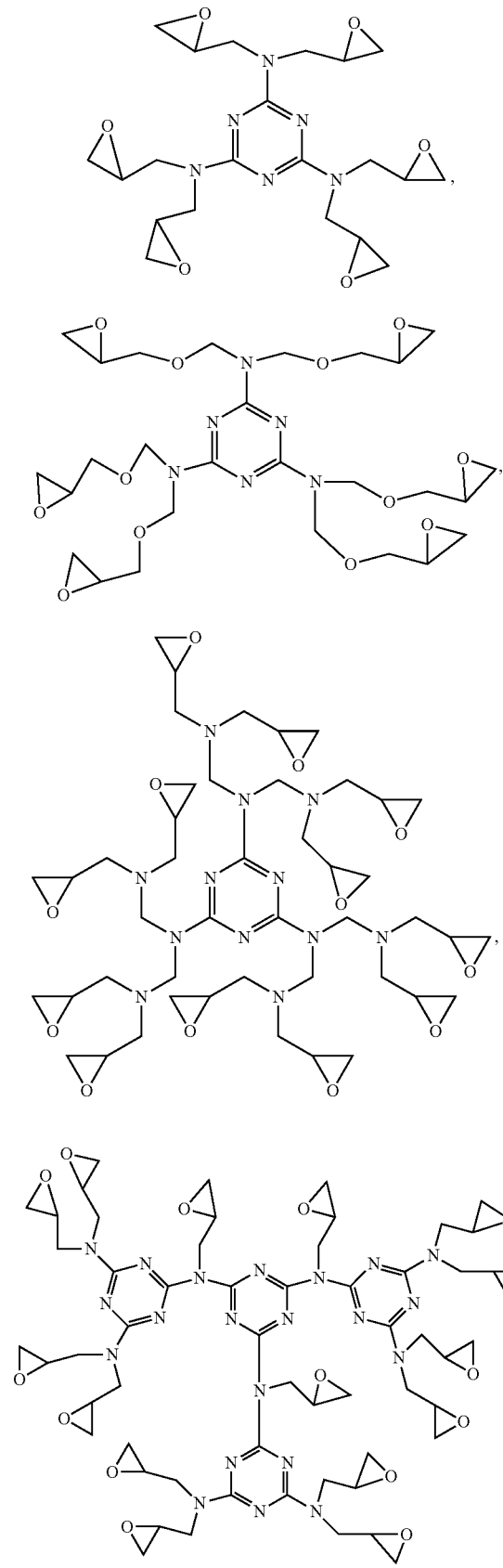

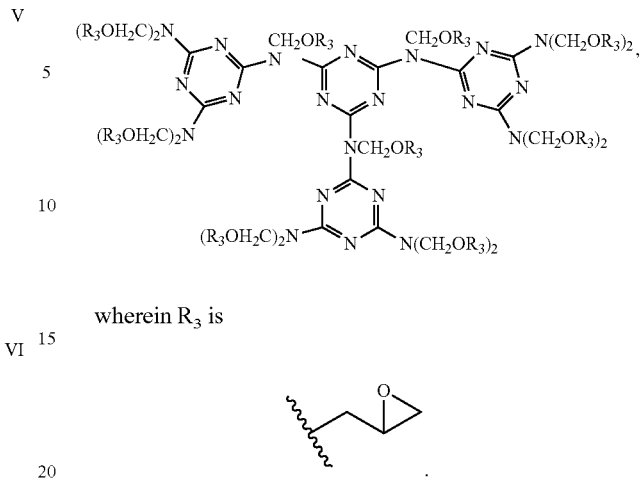

wherein $R_3$ is

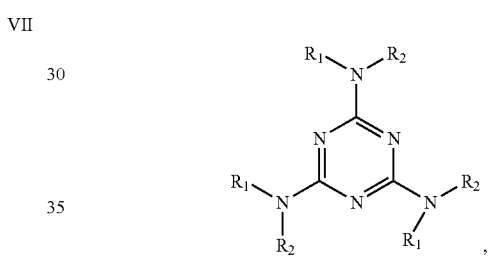

In some embodiments, methods of curing epoxy resins are provided, the methods comprising contacting an epoxy resin disclosed herein with amine compounds, a compound of Formula III

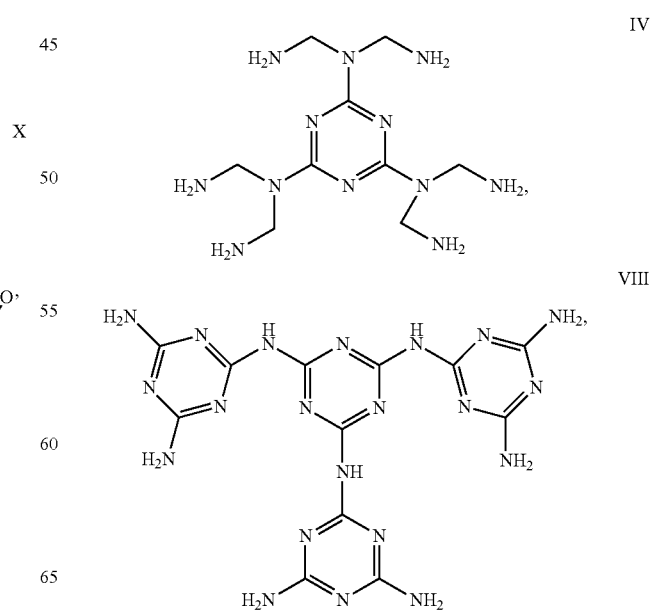

wherein $R_1$ and $R_2$ are independently selected from the group consisting of $CH_2NH_2$, and melaminyl, a compound having a formula of

XIII or with one or more hardeners under conditions sufficient to cure the epoxy resins.

In some embodiments, methods of making a compound of Formula III are provided, the methods comprising contacting hexamethylol melamine with ammonia to produce a compound of Formula IV

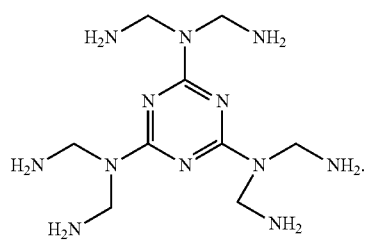

(IV)

In some embodiments, methods of making a compound of Formula V are provided, the methods comprising contacting melamine with epichlorohydrine and a strong base to produce a compound of Formula V

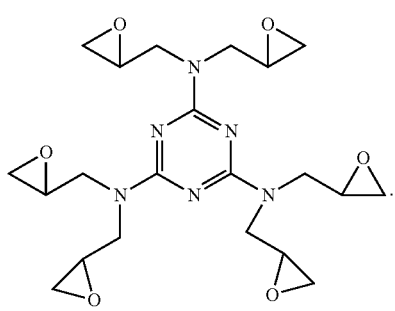

(V)

In some embodiments, methods of making a compound of Formula VI are provided, the methods comprising contacting a compound of Formula II

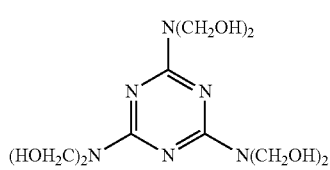

(II)

with epichlorohydrine and a strong base to produce a compound of Formula VI

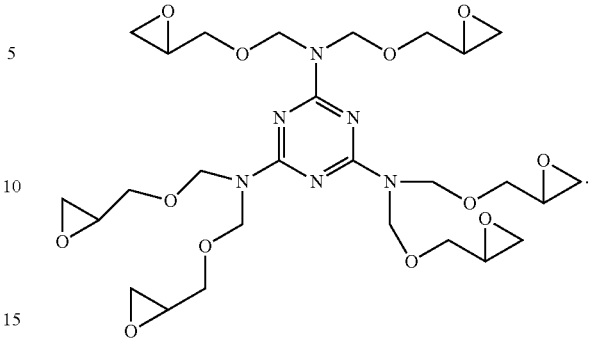

VI

In some embodiments, the method is performed in the presence of a catalyst and co-catalyst. Examples of a catalyst includes, a lewis acid catalyst. The lewis acid catalyst can be, for example, Lanthanium trifluoro-methanesulphonate. Other examples of lewis acid catalysts are known to one of skill in the art. The co-catalyst can be, for example, tetramethylammonium chloride. The co-catalyst can be provided in an aqueous solution, such as a 50% solution in water. Other suitable co-catalysts can also be used.

In some embodiments, methods of making a compound of Formula VII are provided, the methods comprising contacting a compound of Formula IV

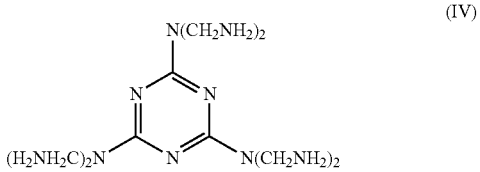

(IV)

with epichlorohydrine and a strong base at a temperature of about 0-80° C. to produce a compound of Formula VII

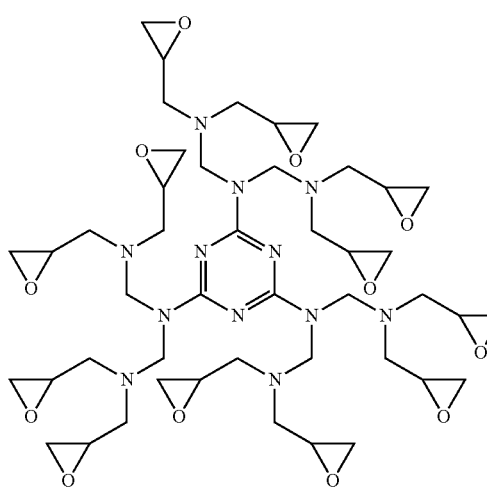

VII

In some embodiments, methods of making a compound of Formula IX are provided, the methods comprising contacting a compound of Formula VIII with excess formaldehyde and a strong base to produce a compound of Formula IX

IX

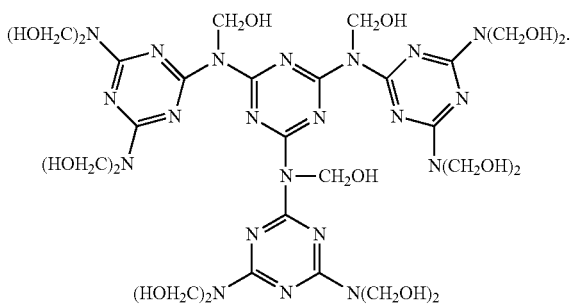

In some embodiments, methods of making a compound of Formula X are provided, the methods comprising contacting a compound of Formula VIII with epichlorohydrine and a strong base at a temperature of about 0-80° C. to produce a compound of Formula X

X

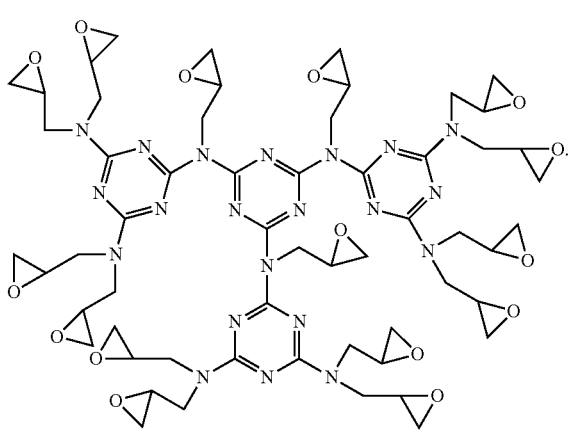

In some embodiments, methods of making a compound of Formula XI are provided, the methods comprising contacting a compound of Formula IX with an excess of epichlorohydrin and a strong base at a temperature of about 50-60° C. to produce a compound of Formula XI

XI

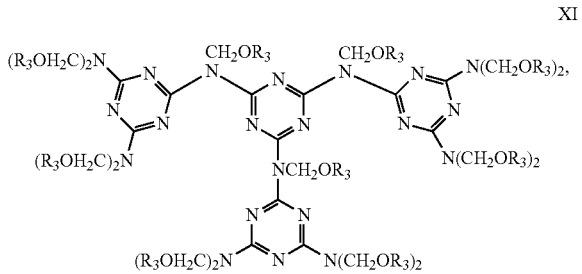

wherein $R_3$ is

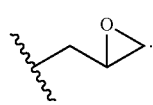

In some embodiments, methods of making a compound of Formula XII are provided, the methods comprising contacting a compound of Formula II with diethanol amine to produce a compound of Formula XII

XII

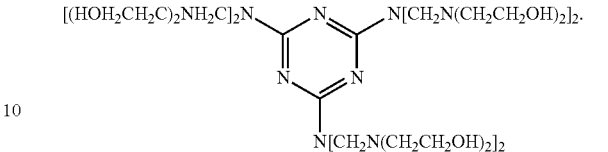

In some embodiments, methods of making a compound of Formula XIII are provided, the methods comprising contacting a compound of Formula XII with ammonia or an aliphatic amine under a pressure of about 1-2 atm to produce a compound of Formula XIII

XIII

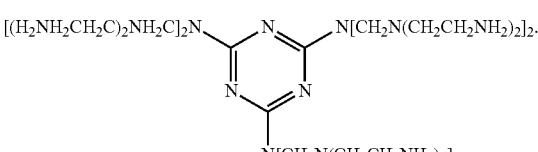

In some embodiments, methods of producing glycidyl ether derivatives of a compound of Formula XII or glycidylamines from any melamine amino derivatives, a compound of formula XIII are provided, the methods comprising contacting a compound of Formula XII or XIII with respectively with epichlorohydrine and a strong base at a temperature sufficient to produce a glycidyl ether derivative from compound of Formula XII or glycidylamines from compound of formula XIII In some embodiments, compositions comprising further generations of melamine derived epoxy resins are provided, the resins prepared by method described herein. In some embodiments, the methods comprise contacting a melamine methylol of Formula II, IX or Formula XII with an amine to produce a melamine amino derivatives; and optionally contacting the melamine amino derivative with an epichlorohydrine to yield glycidylamine derivative; or contacting the melamine amino derivative with formaldehyde and a strong base to yield a methylol derivatives.

DETAILED DESCRIPTION

This description is not limited to the particular processes, compositions, or methodologies described, as these may vary. The terminology used in the description is for the purpose of describing the particular versions or embodiments only, and it is not intended to limit the scope of the embodiments described herein. Unless defined otherwise, all technical and scientific terms used herein have the same meanings as commonly understood by one of ordinary skill in the art. In some cases, terms with commonly understood meanings are defined herein for clarity and/or for ready reference, and the inclusion of such definitions herein should not necessarily be construed to represent a substantial difference over what is generally understood in the art. However, in case of conflict, the patent specification, including definitions, will prevail.

It must also be noted that as used herein and in the appended claims, the singular forms "a", "an", and "the" include plural reference unless the context clearly dictates otherwise.

As used in this document, terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Melamine represents a starting material from which, various resins can be custom designed for many applications including, but not limited to, in various fields of composites, coatings, paints, and Interpenetrating Polymer Networks (IPNs). Melamine has several distinct advantages over existing starting materials. Melamine is a heterocyclic aromatic amine structure, which has been classified as Generally Accepted As Safe (GAAS) (for human uses in industrial applications). All other aromatic amines have been confirmed as carcinogenic to humans and are gradually being phased out of use in Europe and the USA. Additional functionality of the molecule may be achieved with the methods described herein, which will provide the opportunity to use the compounds in many applications and in future uses of resins.

Another advantage of the methods and compounds described herein is that natural sources of melamine exist, which reduces the reliance on petrochemical resources. Therefore, the embodiments provided herein provide an opportunity to utilize melamine obtained from highly industrialized non-petrochemical processes and increase the functionality of the base molecule(s), allowing a range of new possible applications of melamine-based materials.

The compounds and methods described herein are related to the preparation, characterization and evaluation of a series of multifunctional epoxies derived from melamine (Formula I, described herein), methylol melamines (Formula II &XII, described herein), melamine cyanurate (Formula VIII, described herein), methylolic derivatives of melamine cyanurate (Formula IX, described herein) and melamine amine derivatives (Formula IV &XIII, described herein). Some of these have the advantage of being water soluble, which allows them to be used in important applications, such as but not limited to, concrete and water based paint industries.

The multi-functional epoxies also show very high reactivity, which make them highly suitable, such as but not limited to, for photo curing, increasing the degree of crosslinking of commercial epoxy resins, powder coating, and to enhance the epoxy equivalent of ligno epoxy resins. Furthermore, the multi-functional amine derivatives of these raw materials have several outstanding applications, including but not limited to: hardeners, activators, crosslinking agents for polyurethane, silicones, and amino resins. Other advantages, for example, are related to their fire retardant characteristics, high thermal stability, and high glass transition temperatures. Thus, the natural and cost efficient sources of melamine that exist can be exploited that will reduce reliance on petrochemicals and avoid their harmful derivatives.

Melamine can be obtained from any source. It can also be obtained at a relatively reduced cost from urea. Urea, for example, can be industrially produced from synthetic ammonia and $CO_2$. The ammonia by-products of producing melamine from urea can be recycled for production of urea again if desired.

Melamine can also, for example, be sourced from, calcium cyanamide. The hydrolysis of calcium cyanamide in the presence of equal moles of $CO_2$ forms cyanamide, which polymerizes on heating to produce melamine. This process also has an advantage of consuming $CO_2$.

Melamine combined with formaldehyde has been demonstrated industrially to produce melamine formaldehyde resins, which is a durable thermoset used in various applications. Melamine and melamine polyphosphate are also known and used as excellent fire retardant and smoke suppressant additives in paints, plastics and paper. Melamine formaldehyde sulphonate resin (SMF) resins are known to be efficient concrete super-plasticizers. Hexamethylol melamine and its esters and ethers are also known as "melamine oils" are used also as effective crosslinking agents. The following reactions and schema represent novel and non-obvious opportunities for enhancing the properties of melamine based resins and additives and therefore extending its range of use. The compounds and methods described herein can be converted through uncomplicated and cost effective syntheses into a multifunctional epoxies, amines, glycidyl amines and glycidyl amine ethers. The products are valuable multi-functional epoxy resins and hardeners for, but not limited to, composite materials with carbon fibres and/or as cross linking agents for commercial epoxy, polyurethanes, polyesters, and silicones.

The methods, compounds, and compositions provide the following unexpected and surprising advantages over previous compounds used for similar purposes. For example, the compounds and compositions provides herein include, but are not limited to, epoxy resins with multi-functionality that have more than three epoxy groups per molecules and have improved physical, mechanical, and application properties. Additionally, some of the compounds and compositions can be made without the use of petrochemicals. The multi-functional epoxy resins have a higher degree of crosslinking that can lead to higher glass transition and improved resistant to solvents and corrosive chemicals. The Multi-functional epoxy (MFE) based on melamine are self-extinguishing products with outstanding fire retardant properties due to presence of melamine structures. These products are different from melamine formaldehyde resins. Some of the MFE epoxy amino derivatives or amino hardeners also have improved water miscibility than common aromatic epoxy. Therefore, these resins are suitable for applications in humid environments, wet surfaces, and water based epoxy for construction and water based paints. However, when they are cured with suitable hardeners they are completely water and solvent resistant. Thus, the compounds and compositions described herein have expanded uses as compared to the prior art. The compounds and compositions described herein can also be used as improved cross linking agents and/or fire retardants.

Accordingly, in some embodiments, compounds having the structure of Formula III

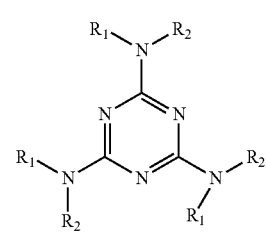

III are provided. In some embodiments, $R_1$ and $R_2$ are each independently selected from the group consisting of:

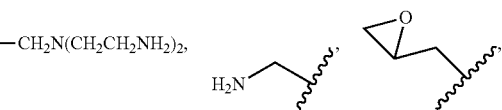
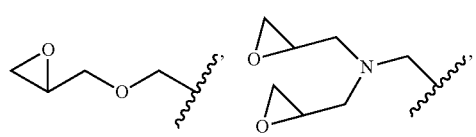
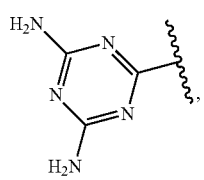 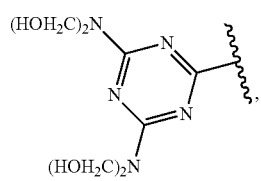
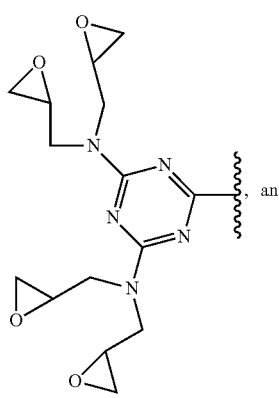 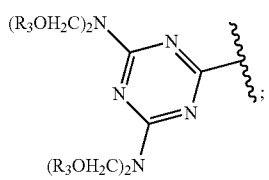
wherein $R_3$ is
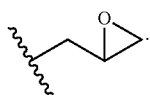 [SMILES: *CC1CO1].
In some embodiments, when $R_1$ is H, $R_2$ is not H or —$CH_2OH$.
In some embodiments, when $R_1$ is
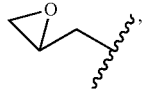 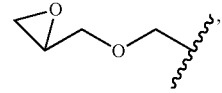
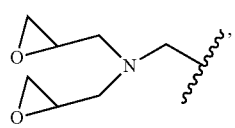 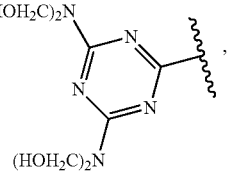
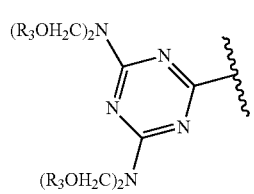
$R_2$ is not
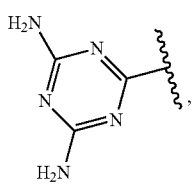, —$CH_2N(CH_2CH_2NH_2)_2$, or
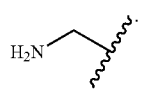.
In some embodiments, when $R_1$ is H, $R_2$ is not —$CH_2OR_3$.
In some embodiments, $R_1$ and $R_2$ are the same.
In some embodiments, compounds having the formula of:
IV
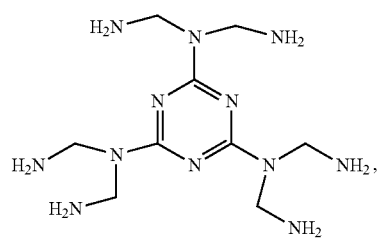
V
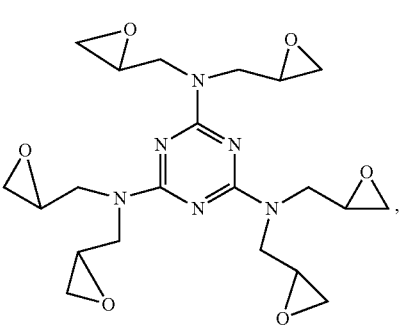

-continued
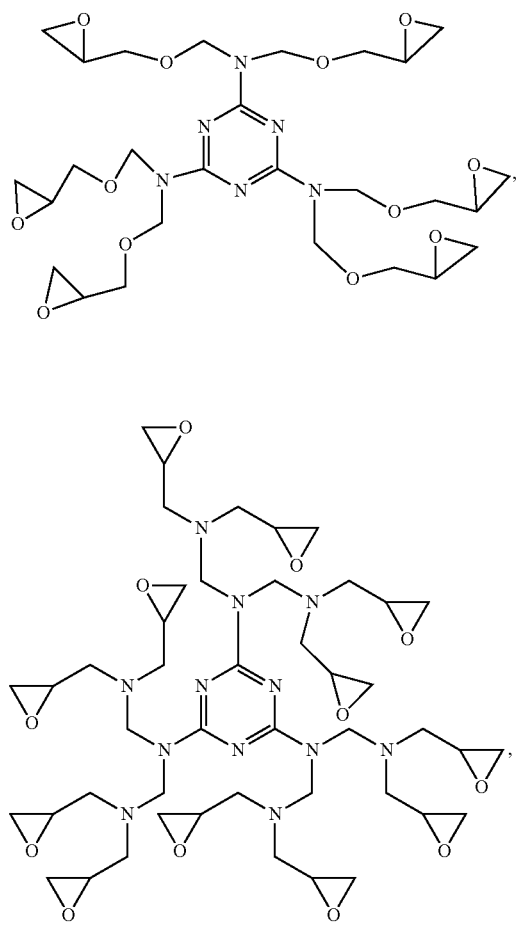
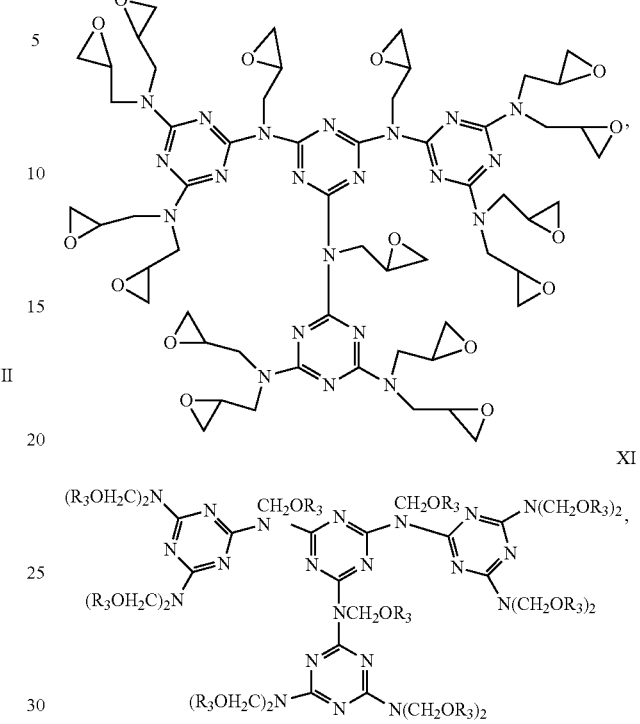
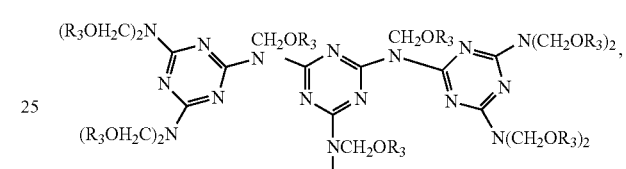
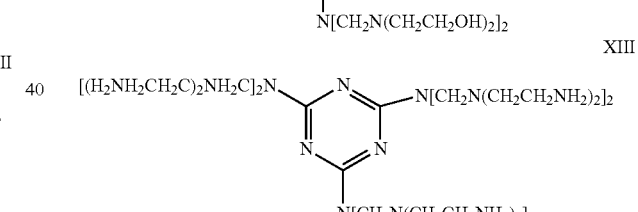
are provided.
In some embodiments, a composition comprising one or more of the compounds having the formula of Formula III are provided:
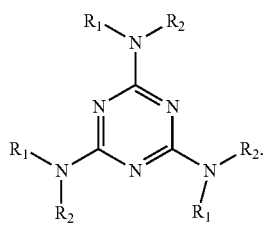
In some embodiments, $R_1$ and $R_2$ are each independently selected from the group consisting of: H, —$CH_2OH$, —$CH_2OR_3$, —$CH_2N(CH_2CH_2OH)_2$, —$CH_2N(CH_2CH_2NH_2)_2$,

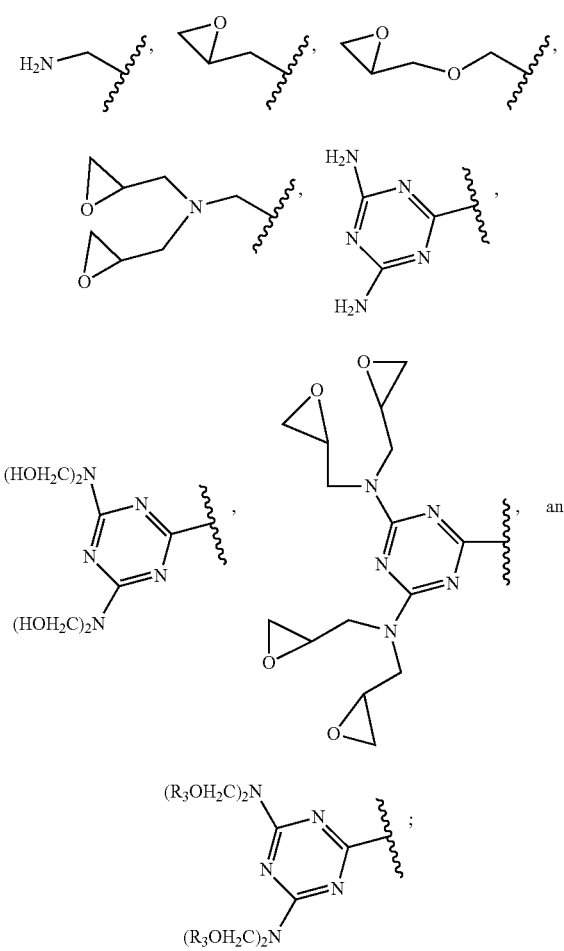

wherein $R_3$ is

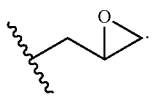 [SMILES: *CC1CO1]

In some embodiments, when $R_1$ is H, $R_2$ is not H or —$CH_2OH$.

In some embodiments, when R1 is

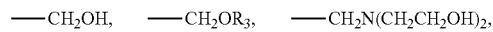

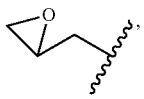 , 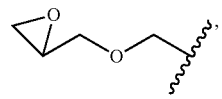 ,

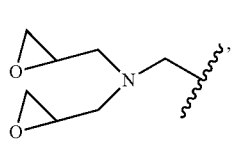 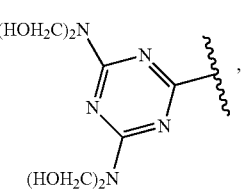

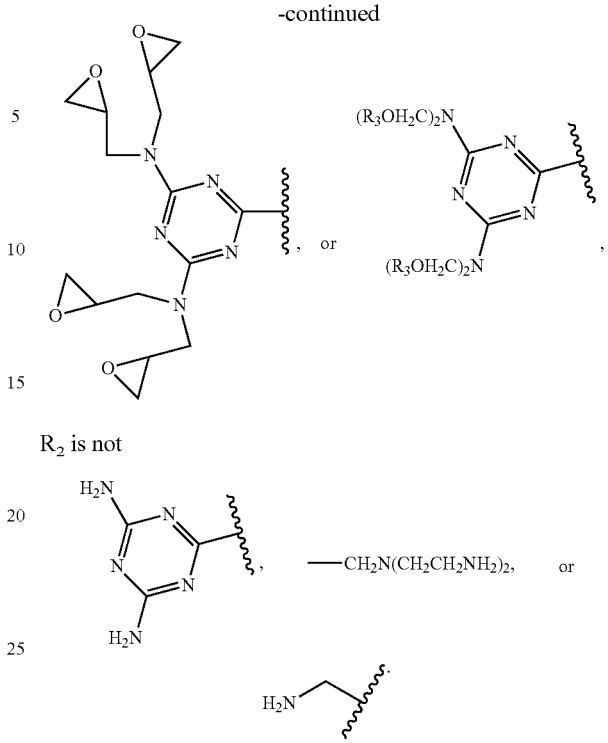

$R_2$ is not

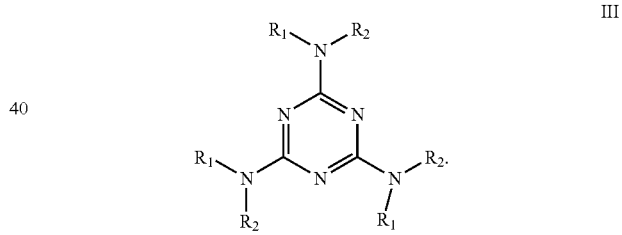

In some embodiments, $R_2$ does not comprise a terminal amino group.

In some embodiments, an epoxy resin is provided. In some embodiments, the epoxy resin comprises a compound having the structure of Formula III:

III

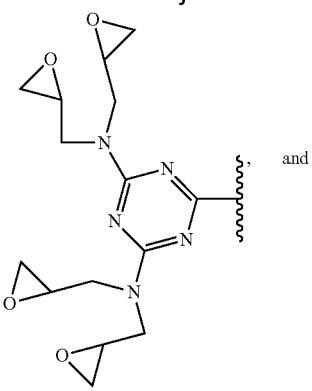

In some embodiments, $R_1$ and $R_2$ are each independently selected from the group consisting of epoxy groups

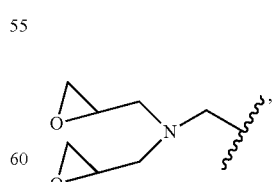

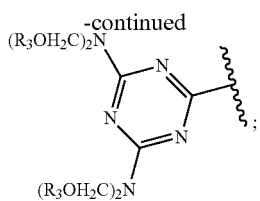

wherein $R_3$ is

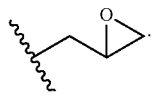

In some embodiments, when $R_1$ is H, $R_2$ is not H or —$CH_2OH$. In some embodiments, when $R_1$ is

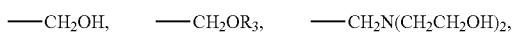

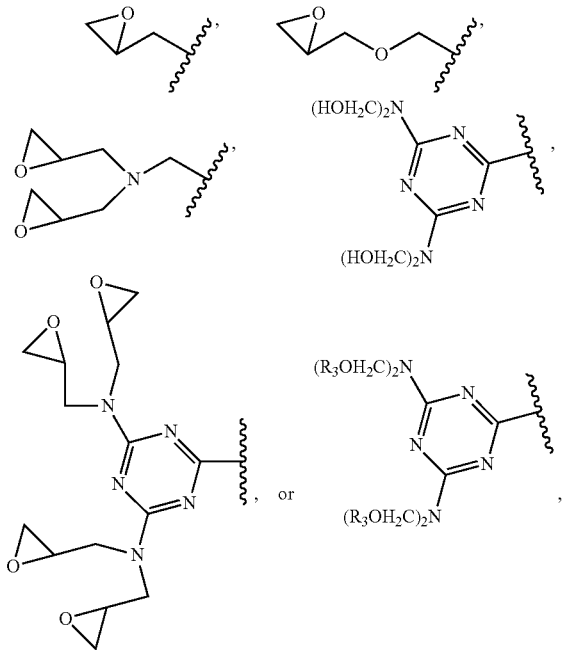

$R_2$ is not

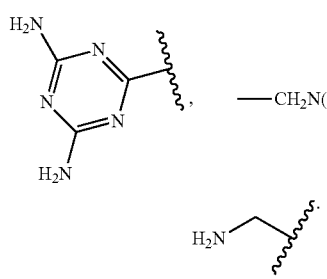

In some embodiments, carbon fibers or carbon fiber composites are provided. In some embodiments, the fiber or composite comprises a cured epoxy resin, which comprises an epoxy resin and amino hardeners. In some embodiments, the carbon fiber comprises a cured epoxy resin with suitable hardeners. In some embodiments, the epoxy resin is a compound of Formula III

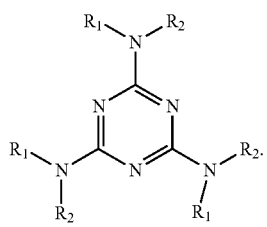

In some embodiments, $R_1$ and $R_2$ are independently selected from the group consisting of

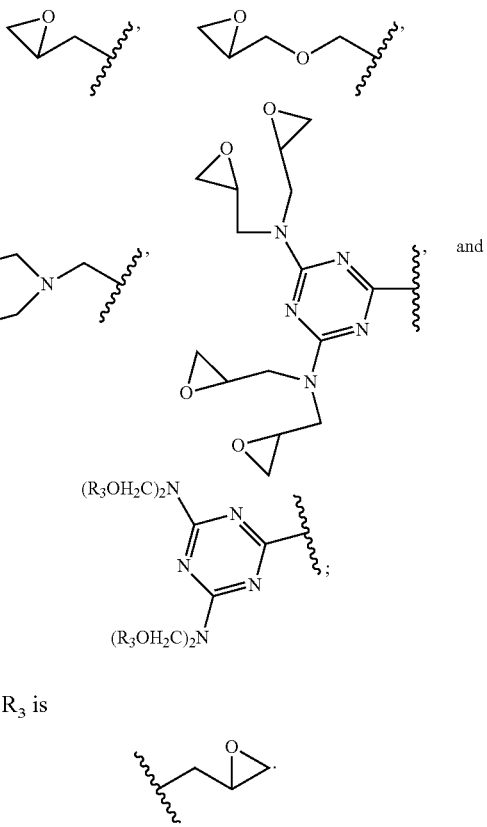

wherein $R_3$ is

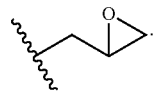

In some embodiments, the carbon fiber composite has an epoxy resin that has a Formula of

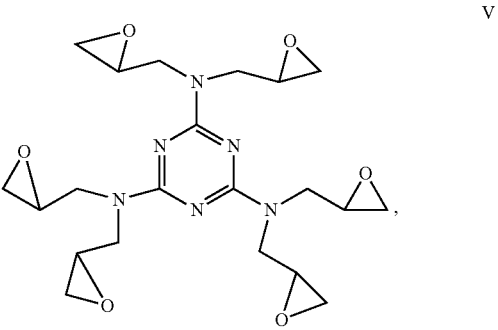

-continued

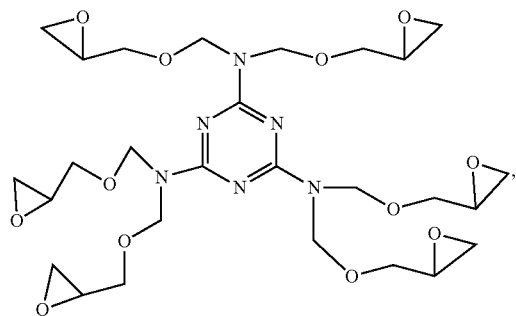
VI

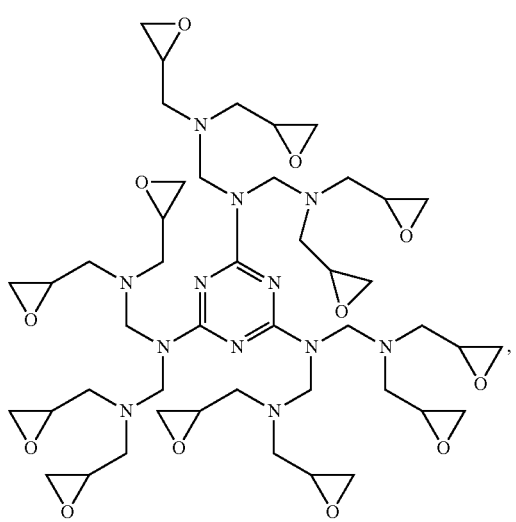
VII

X

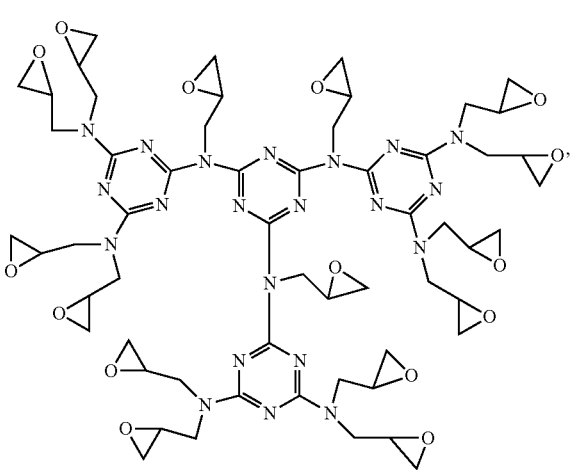

XI

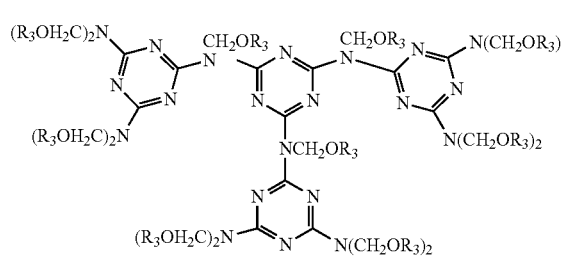

wherein $R_3$ is

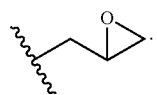

In some embodiments, the hardener has a compound of Formula III. In some embodiments, the resin comprises any melamine amino derivatives such as, but not limited to, a compound of Formula IV, VIII, or XIII In some embodiments, cross-linked polyurethanes, polyester, or silicone are provided, wherein the polyurethane, polyester, or silicone are cross-linked with a compound of Formula III

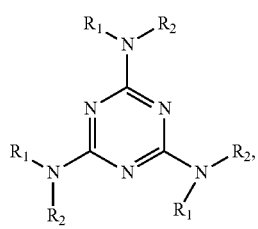
III wherein $R_1$ and $R_2$ are independently selected from the group consisting of H, $CH_2OH$ $CH_2NH_2$, and melaminyl, or are cross-linked with a compound having a formula of

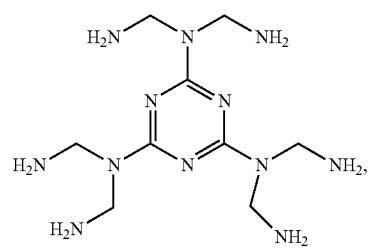
IV

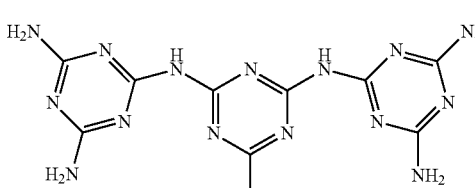
VIII

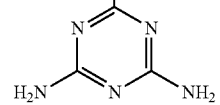

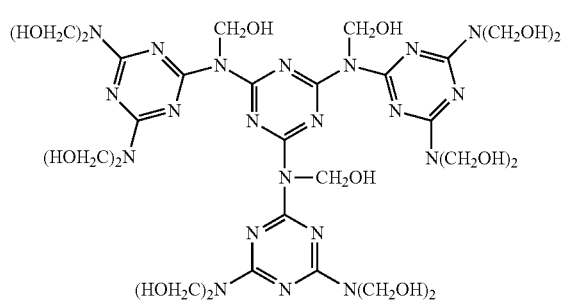
IX
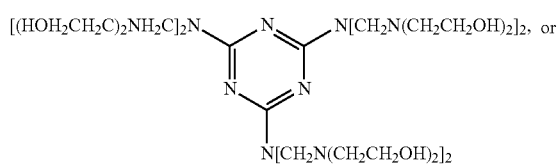
XII
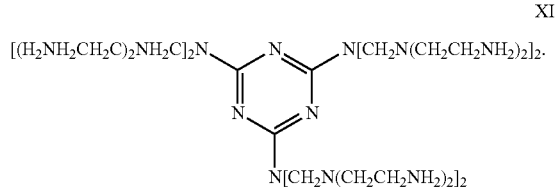
XIII
In some embodiments, a composite comprising one or more of a cured epoxy resins with suitable hardeners, wherein the epoxy resin is a compound of Formula III
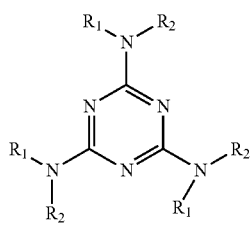
III
are provided. In some embodiments, $R_1$ and $R_2$ are independently selected from the group consisting of:
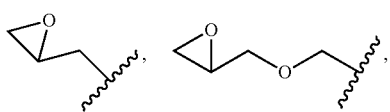
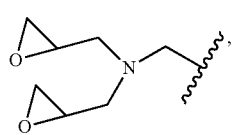
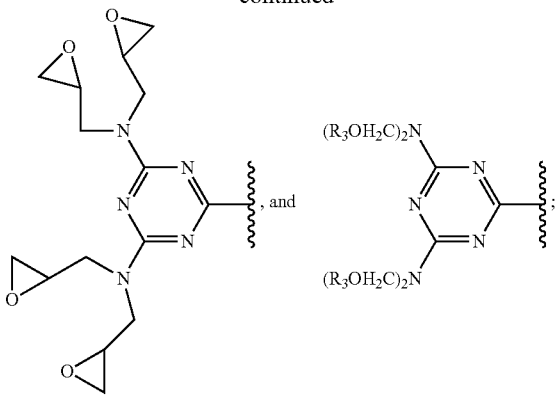
and $R_3$ is
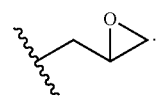
In some embodiments, the epoxy resin has a Formula of
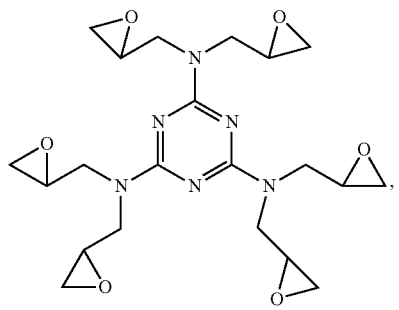
V
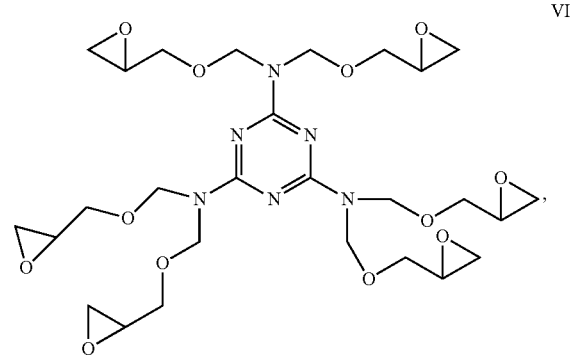
VI -continued

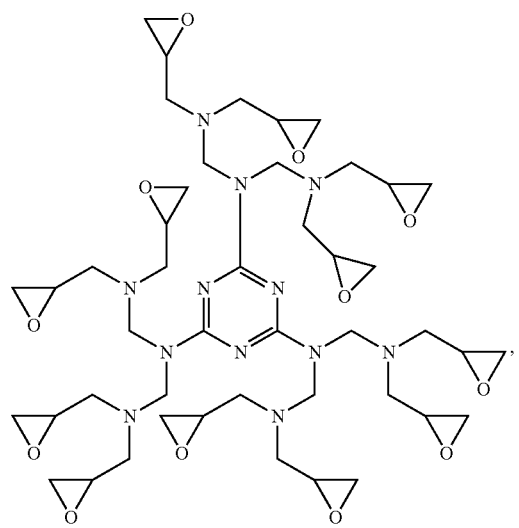

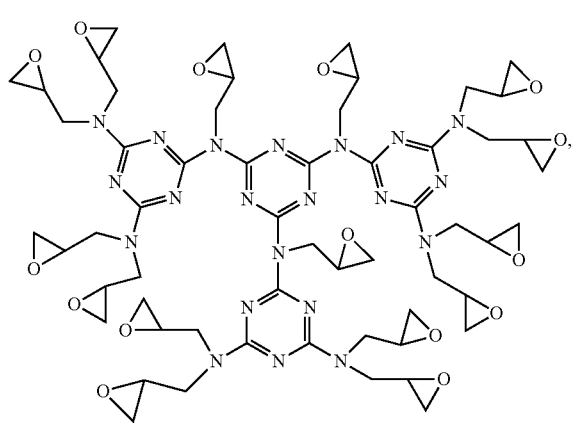

wherein $R_3$ is

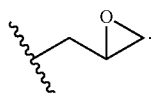

In some embodiments methods of curing an epoxy resin are provided. In some embodiments, the method comprises contacting the epoxy resin or the polyurethane resins terminated with isocyanate groups such as polyester polyol terminated with isocyanate active groups with an amine compound, a compound of Formula III

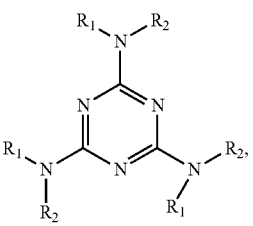

wherein $R_1$ and $R_2$ are independently selected from the group consisting of H, $CH_2OH$ $CH_2NH_2$, and melaminyl, a compound having a formula of

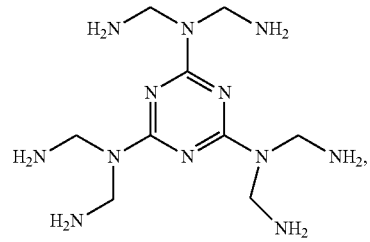

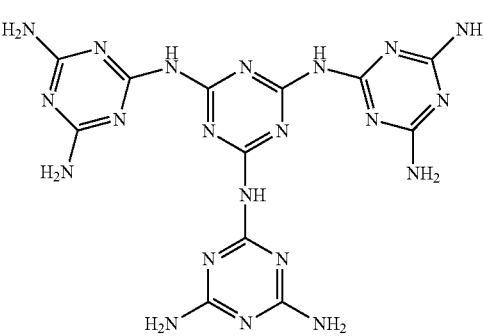

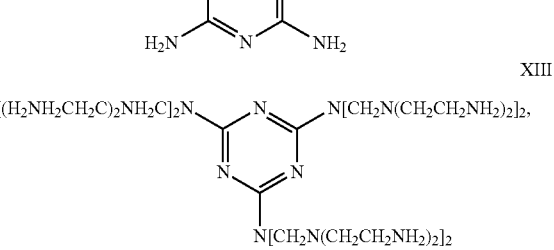

or with one or more commercial hardeners under conditions sufficient to cure the epoxy resin.

In some embodiments, methods of making a compound of Formula III are provided. In some embodiments, the method comprises contacting hexamethylol melamine II with ammonia to produce a compound of Formula IV

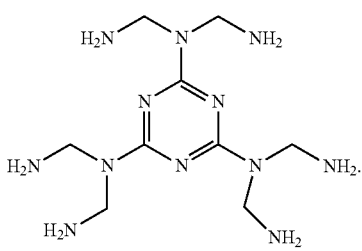

In some embodiments, methods of making a compound of Formula V are provided. In some embodiments, the methods comprises contacting melamine with epichlorohydrine and a strong base (e.g. sodium hydroxide or potassium hydroxide) to produce a compound of Formula V

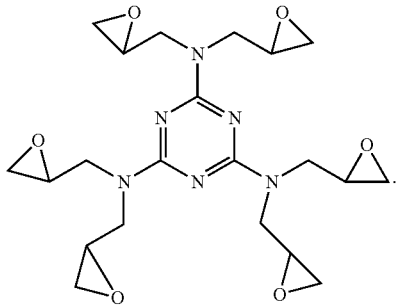

(V)

In some embodiments, the method is performed at a temperature of about 0-80° C. In some embodiments, the method of making a compound of Formula V is performed at three temperature stages: a temperature of about 0-10° C. for the initial reaction of epichlorohydrine with melamine and its derivatives for the first stage, about 40-80° C. for the second stage and about 50-65° C. for final dehydrochlorination stage. In some embodiments, the method of making a compound of Formula V is performed at a temperature from about 0-80° C.

In some embodiments, methods of making a compound of Formula VI are provided. In some embodiments, the methods comprise contacting a compound of Formula II

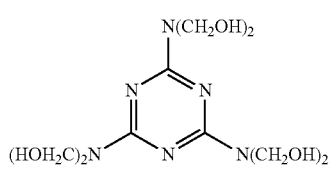

(II)

with epichlorohydrine and a strong base (e.g. sodium hydroxide potassium hydroxide, and the like) to produce a compound of Formula VI

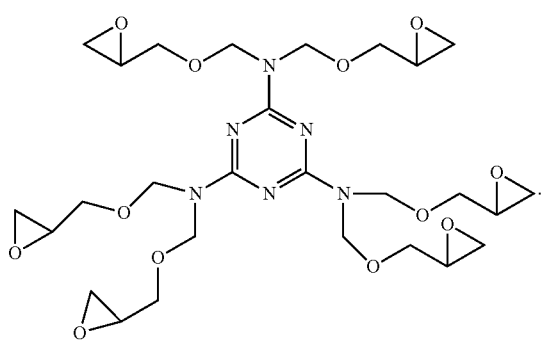

VI

In some embodiments, the method is performed at temperature of about 50-60° C.

In some embodiments, methods of making a compound of Formula VII are provided. In some embodiments, the methods comprise contacting a compound of Formula IV

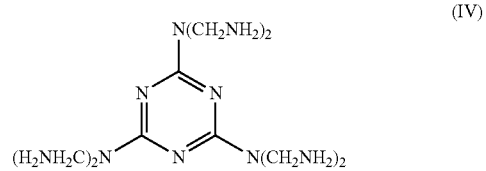

(IV)

with epichlorohydrine a strong base (e.g. sodium hydroxide potassium hydroxide, and the like) at a temperature of about 0-80° C., including, for example, at three different temperature stages as described herein, to produce a compound of Formula VII

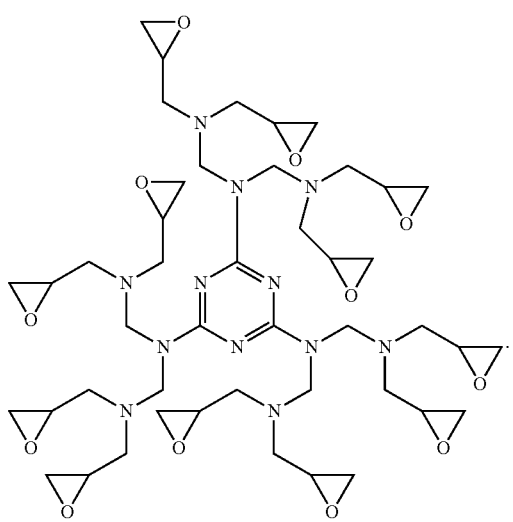

VII

In some embodiments, the method comprises contacting melamine with cyanuryl chloride to produce a compound of Formula VIII.

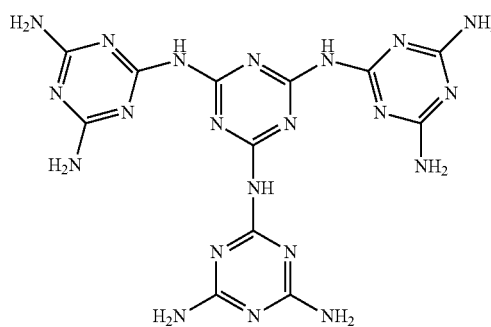

VIII

In some embodiments, methods of making a compound of Formula IX are provided. In some embodiments, the methods comprise contacting a compound of Formula VIII with excess formaldehyde with a strong base (e.g. sodium hydroxide potassium hydroxide, and the like) to produce a compound of Formula IX

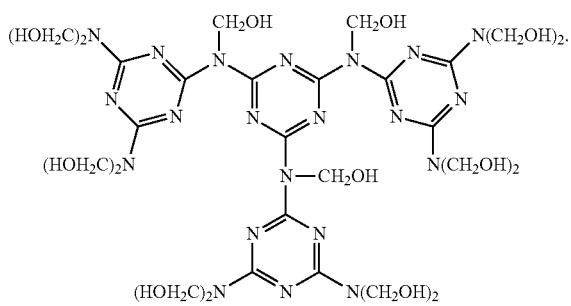

IX

In some embodiments, methods of making a compound of Formula X are provided. In some embodiments, the methods comprise contacting a compound of Formula VIII with epichlorohydrine and a strong base, such as, but not limited to, sodium hydroxide or potassium hydroxide at a temperature of about 0-80° C., including, for example, at three different temperature stages as described herein to produce a compound of Formula X

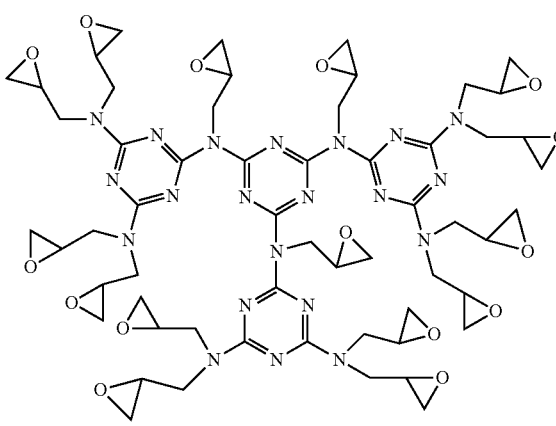

X

In some embodiments, methods of making a compound of Formula XI are provided. In some embodiments, the methods comprise contacting a compound of Formula IX with an excess of epichlorohydrine and a strong base (e.g. sodium hydroxide potassium hydroxide, and the like) at a temperature of about 50-60° C. to produce a compound of Formula XI

XI

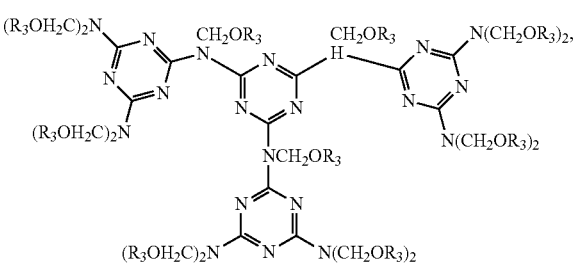

wherein $R_3$ is

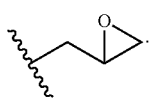 [SMILES: *CC1CO1]

In some embodiments, methods of making a compound of Formula XII are provided. In some embodiments, the methods comprise contacting a compound of Formula II with diethanol amine to produce a compound of Formula XII

XII

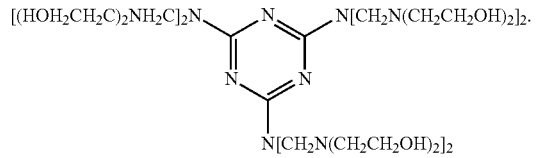

In some embodiments, methods of making a compound of Formula XIII are provided. In some embodiments, the method comprises contacting a compound of Formula XII with ammonia or an aliphatic amine under a pressure of about 1-2 atm to produce a compound of Formula XIII

XIII

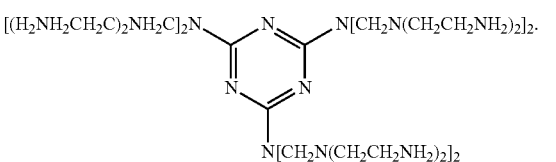

In some embodiments, methods of producing glycidyl ether derivatives from a melamine methylol derivative, such as but not limited to Formula XII or glycidylamines from a melamine amino derivatives, such as a compound of formula XIII (as an example of any melamine amino derivatives) are provided. In some embodiments, the methods comprise contacting a compound of, for example, Formula XII or XIII, respectively, with epichlorohydrine and a strong base (e.g. sodium hydroxide potassium hydroxide, and the like) at a temperature sufficient to produce a glycidyl ether derivative from compound of Formula XII or glycidylamines from compound of formula XIII.

A composition comprising further generations of melamine derived epoxy resin, the resin prepared by a method, the method comprising contacting a compound melamine methylols of formula II, IX or Formula XII or other melamine methylols with an ammonia or an amine to produce new melamine amino derivatives which could be either transferred to glycidylamine derivatives similar to V, VII, or X, as an example, by their direct reactions with an epichlorohydrine or to be transferred to new generation of methylol derivatives by their reaction with formaldehyde and a strong base similar to II, IX and XII, as an example. The new generation of methylols could be either transferred to their glycidylether derivatives or transferred to amino groups again to form the next generation of melamine amino derivatives. This can be continued for several sequences mainly for producing powder solid epoxy for spray powder technology coating with epoxy resins. The limit of the sequence of generations is when the product is insoluble and/or infusible.

EXAMPLES

Example 1

Preparation of Resin II: Hexa Methylol Melamine

Hexamethylolmelamine was prepared and characterized according to (Manley, T. R, Thermalstability of hexamethylolmelamine, Polymer, J. 4, (1)111-113, 1972) Three necked reaction vessel fitted with reflux, thermometer condenser and mechanical stirrer. The reaction vessel was charged with 126 g melamine (1 mole), and 650 g (8 moles) forlmaline solution 37%. 10% sodium carbonate solution was added (pH 8.5-9). The solution was heated to 65-70° C. for 3 hours with continuous efficient mixing after 3 hours the reaction mixture became transparent indicating that all melamine was transferred to its methylolic resins. The product was cooled to room temperature and excess of non reacted formaldehyde was removed. The solid product was used in the preparation of the new melamine derivatives of this invention. A modified procedure was also used by using sodium hydroxide as basic medium for the reaction.

Example 2

Preparation of Hexa Aminomelamine: Resin III where R1, R2 are NH2 (Compound IV)

A two liter auto clave system from Analis-Belgium fitted with mechanical stirrer, and controlled temperature and pressure was charged with 306 g hexamethylol melamine prepared in Example 1 and 500 ml of methyl alcohol. The system was secured and connected to ammonia gas cylinder. The system was flashed with N2, mixed for 10 minutes to dissolve the methylol resin. Ammonia gas was fed to the autoclave until the pressure reached 2 atm. The reaction temperature was controlled at 50-60° C. via the cooling jacket of the autoclave. The reaction was continued until no further increase in temperature was observed. The system was cooled to room temperature. The system was flushed with $N_2$ gas to remove the unreacted ammonia gas. The white milky syrup product was evaporated and dried under vacuum. The solid product with a decomposition temperature of 387° C. was obtained. The product characterized by CHN analysis and molecular weight determination.

The obtained degree of amination as found from CHN analysis was 87%. The obtained resin was used in the preparation of glycidyl melamine resins as an epoxy hardener, as a crosslinking agent for polyurethane, as curing agent for: methylol melamine, resol, resolack, and as starting material for the second generation of melamine methylol derivatives compounds XII and XIII (Example 10).

Example 3

Preparation of N-Glycidyl Melamine Resins: Resin III where R1, R2 are Glycidyl Groups Compound (V)

A reactor consisting flanged top five necked reaction vessel fitted with: a mechanical stirrer, condenser, thermometer, dropping funnel, gas inlet tube, immersed in thermo stated oil bath. The reaction vessel was charged with 63 g melamine (0.5 mole) dissolved in 100 DMF one gram of Mg ($ClO_4$) dissolved in 5 ml 2-methoxy ethanol was added as catalyst. The system was flashed with nitrogen for 10 minutes and the reaction mixture was cooled to 10° C. 350 ml of epichlorohydrin was added to the reaction mixture portion wise over one hour with continuous mixing for another 60 min then the temperature was increased gradually up to 60° C. and the reaction was continued for an additional three hours with the temperature controlled between 60-80° C. The reaction mixture was cooled to 65° C. 12 g of tetra butyl ammonium chloride dissolved in 25 ml water was added with mixing followed by the addition of 250 ml of 50% sodium hydroxide solution, which was added portion wise with continuous efficient mixing over two hours. The mixture was heated to 70° C. for two hours. The reaction mixture was cooled to room temperature then the formed resin was separated by addition of 100-200 ml of water with mixing to ensure that all the epoxy product is separated from DMF. The epoxy layer was separated, dissolved in toluene, filtered from any salt residue and washed with 40% solution of sodium chloride in water containing 1% acetic acid, dried with molecular sieves, evaporated under vacuum and dried under vacuum at 0.1 mm Hg at 40° C. for 6 hours. A dark colored viscous resin was obtained. The epoxy equivalent of the resin was determined and found to be 5.34 equivalent/kg, viscosity at 40° C. was 91.4 Pa s, and active chlorine content (0.3%).

Example 4

Effect of Metal Salt Catalysts

The procedure of Example 1 was repeated in the absence of catalyst and in the presence of LiCl, LiOH, and $LiClO_4$ catalysts. No appreciable changes were found in the yield of epoxy equivalent and viscosity by changing the catalyst. The absence of catalysts reduces the epoxy equivalent to 4.5 equivalent/kg and increases the viscosity of 110 Pa s.

Example:5

Effect of Phase Transfer Co Catalyst

Example 1 was repeated in the presence of several phase transfer catalysts, e.g. benzyltrimethylammonium bromide, cetyltrimethylammonium bromide, tetrabutylammonium hydroxide. No appreciable changes were found in the: yield, epoxy equivalent and viscosity. The absence of phase transfer catalyst reduces the epoxy equivalent of the resin to 4.1 equivalent/kg and increases the viscosity to 95 Pa s.

Example-6

Effect of Temperature

Several reaction schemes were implemented at various temperatures from zero to 100° C. It was found that the initial stage of addition of epichlorohydrine to melamine solutions in the presence of catalysts was highly exothermic when the reaction was fulfilled at temperatures above 50° C. which lead to formation of water soluble polymelamine epichlorohydrine polycondensate. The three stage temperature control presented in Example 1 was found to give the highest epoxy equivalent, lowest viscosity and lowest active chlorine content (0.3%).

Example 7

Preparation of Hexamethylolmelamineglycidyl Ether (Compound VI)

The reaction set up used in Example 3 was used. The reaction vessel was charged with 153 g (0.5 mole)hexamethylol melamine prepared in Example 1 and 250 ml of n-butanol. The mixture was neutralized with benzene sulphonic acid to pH-7-7.5. The system was flashed with $N_2$ for 10 minutes. 0.75 g Lanthaniumtrifluoro-methanesulphonate was added as lewis acid catalyst and 5 g of tetra methylammonium chloride as a 50% solution in water. The system was heated to 50° C. 323.8 g (3.5 mole) of epichlorohydrine was added within 2 hours and then the mixture was heated to 75° C. for one hour. The mixture was cooled to 60° C. and then 280 g (3.5 mole) of 50% sodium hydroxide solution was added portionwise within one hour with continuous azeotropic removal of water from the system and with continuous mixing for further one hour at 60 C. The reaction mixture was cooled to room temperature. The solid residue was found to be crosslinked melamine resin and salt. Butanol was evaporated under vacuum. Highly viscous resin was obtained (epoxy equivalent 5.56 mol/kg, chlorine content was 1.9%, yield based on melaminehexamethylol resin was 72%).

Example 8

Preparation of the Second Generation of Glycidyl Melamine Amino Resins (Compound VII)

The same procedure used in example 3 is implemented but replacing melamine by hexaaminomelamine (resin IV) doubling the molar ratio of epichlorohydrine, catalyst, co-catalyst, and sodium hydroxide. The catalyst and co-catalyst are the same as were used in Example 7. The expected reaction product is solid epoxy resin with much higher epoxy equivalent than resin (V).

Example-9

Preparation of the N-Glycidyl Melamine Cyanurate (Compound X)

The same procedure used in example 3 is implemented but replacing melamine by melamine cyanurate (resin VIII) using the molar ratio of epichlorohydrine, catalyst, co catalyst, and sodium hydroxide equivalent to the number of the amino groups present in resin VIII. The catalyst and co-catalyst are the same as were used in Example 7. The expected reaction product is solid epoxy resin with much higher epoxy equivalent than resin (V).

Example 10

Preparation of Melamine Cyanuratemethylol Resin: (Compound IX)

The set up and procedure of Example 1 is used in the preparation of resin IX by using molar ratio of formaldehyde/amino as 2.2:1 using the same catalysts and reaction conditions. The expected melamine cyanurate methylol resin is waxy solid product.

Example 11

Preparation of Melamine Cyanurateglycidyl Ether: (Compound XI)

(Proffitic) The set up and chemicals used in Example 7 for preparation of melamine derivative glycidylether (compound VI) are used in the preparation of the melamine cyanurate glycidylether (compound XI) by replacing resin II by resin IX implementing the same procedure at the same reaction conditions and using the same molar ratio of epichlorohydrin: methylol:NaOH taking into consideration the number of methylol groups in compound IX. The product epoxy resin is solid with higher epoxy equivalent.

Example 12

Curing of Glycidyl Melamine Resin

A) 10 g of glycidylmelamine (IV) was cured with 3.5 grams of melamine mixed and cured at 80° C. for 16 hours. The resin was found cure to solid tough product with a glass transition temperature of 172° C. as measured by DSC. The sample at room temperature did not cure completely but the viscosity increased remarkably, which is an indication for partial curing at ambient temperature. B) 10 g of glycidylmelamine (IV) was cured with 2.5 g of hexa amino melamine (III). The sample underwent curing at room temperature and at 60° C. The post cured sample had a glass transition temperature of 187° C. C) 10 g of glycidylmelamine (IV) was cured with 2.5 g of amino melamine (VII). The sample underwent curing at room temperature and at 60° C. The post cured sample had a glass transition temperature of 174° C. D) 10 g of glycidyl melamine (IV) was cured with 3.5 g of Huntsman commercial curing agent 1203, the resin cured to solid product at room temperature. The post cured sample had a glass transition temperature of 175° C.

Example 13

Curing of Melamine Glycidylether (VI)

10 g of melaminehexamethylolglycidyl ether (VI) was cured with equivalent ratios of the amino resins tested in Example 12. Compounds I, III, VII and Huntsman 1203 is a standard commercial hardener, which have hardener equivalent weights of 114 g/equivalent. The sample underwent curing at room temperature and at 60° C. with all curing agents except with compound I. The glass transition for the post cured sample Compound VI in the presence of compounds I, III, VII or Huntsman 1203 of was 168, 175, 177 and 168° C., respectively as measured by DSC at 10 degrees/minute.

Example 14

Crosslinking and Catalytic Efficiency of Melamine Amino Derivatives and Melamine Methylol Resins A) Commercial polyether polyol terminated with isocyanate (10 g) liquid component was mixed with one gram of melamine amino resins IV. A solid polyurethane foam was formed instantly. The density of the foamed product, which is very important in polyurethane technology, can be controlled by the ratio of the aminocrosslinking agent added. B) Commercial polyether polyol terminated with isocyanate (10 g) liquid component was mixed with one gram of melamine methylol resins II. A flexible polyurethane foam was formed instantly.

What is claimed is:

1. A carbon fiber composite comprising a cured epoxy resin of an epoxy resin and amino hardeners, wherein the epoxy resin is a compound of Formula III

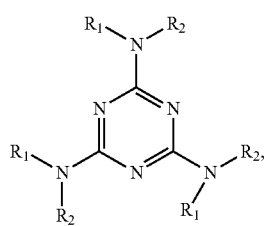
wherein $R_1$ and $R_2$ are independently selected from the group consisting of:
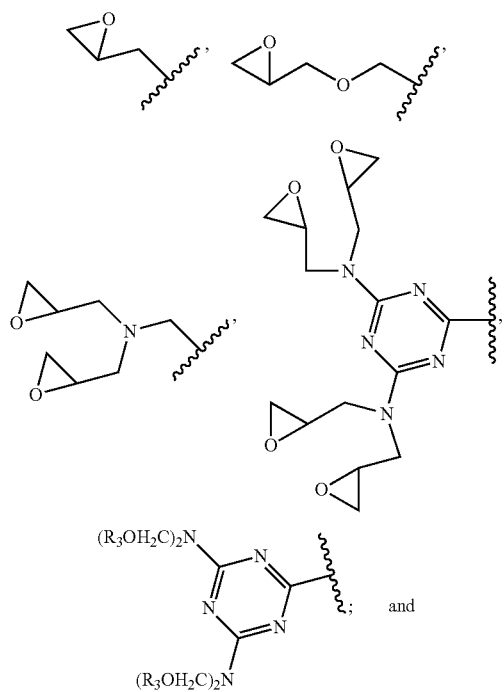
$R_3$ is
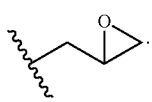 [SMILES: *CC1CO1]
2. The carbon fiber composite of claim 1, wherein the epoxy resin has a Formula of
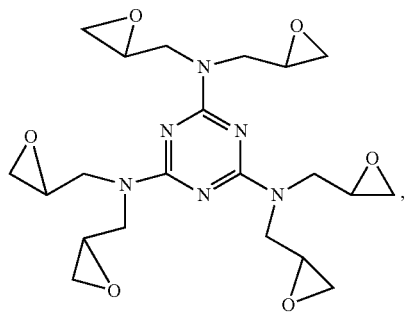
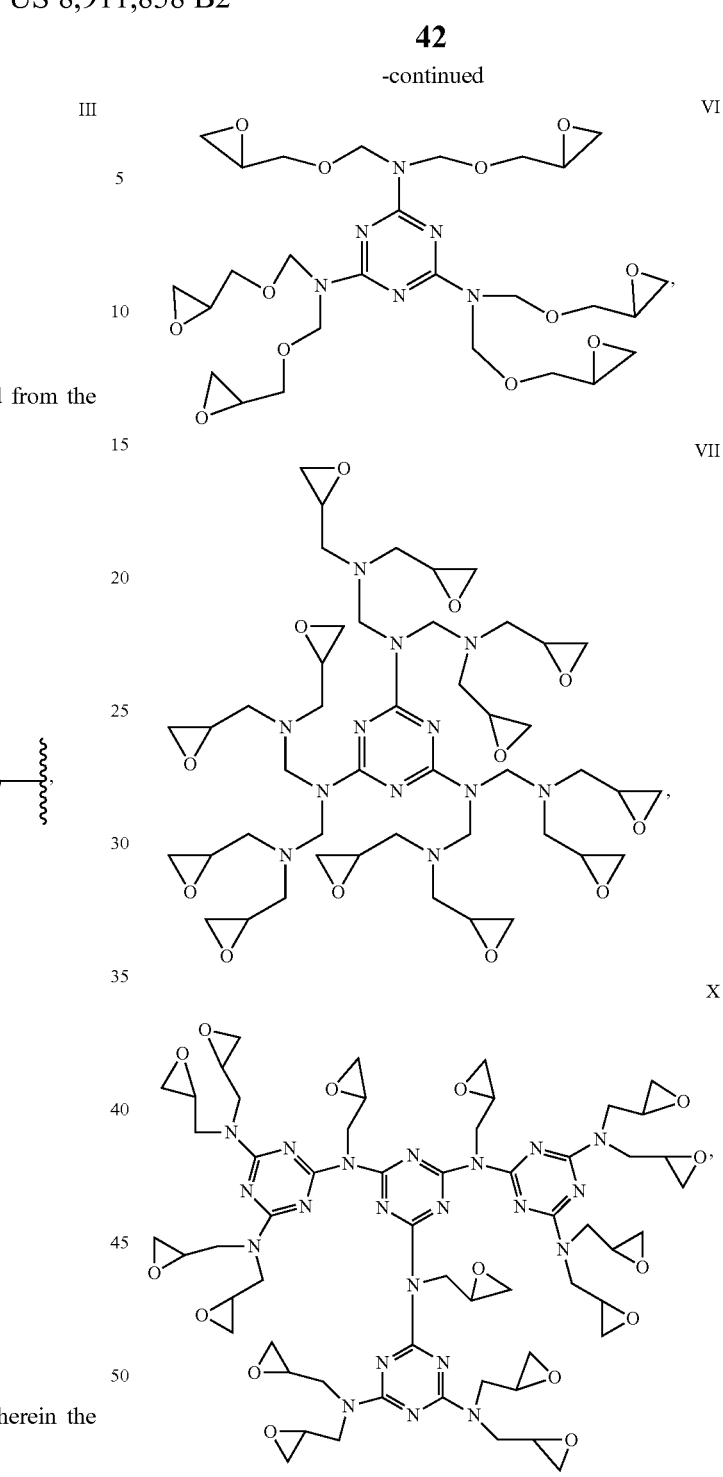
or
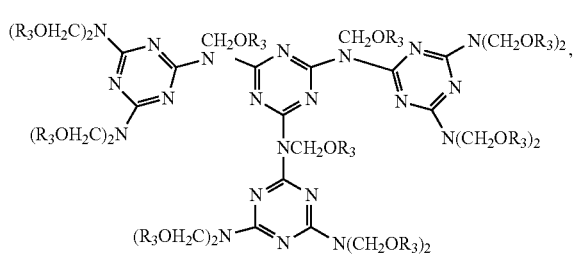

wherein $R_3$ is

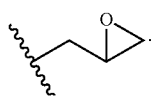

3. The carbon fiber composite of claim 2, wherein the epoxy resin has a Formula of

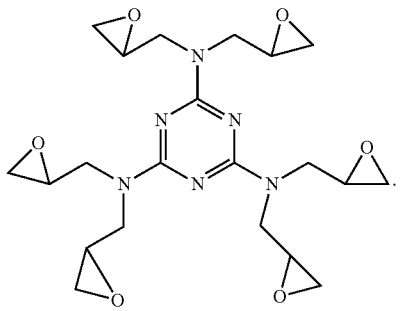
(V)

4. The carbon fiber composite of claim 2, wherein the epoxy resin has a Formula of

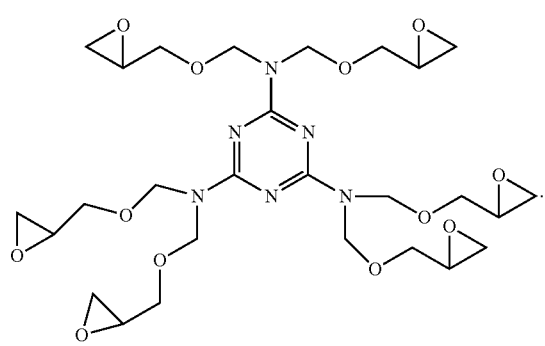
VI

5. The carbon fiber composite of claim 2, wherein the epoxy resin has a Formula of

VII

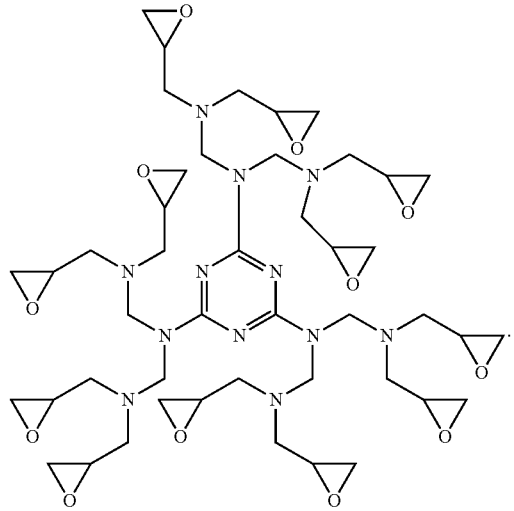

6. The carbon fiber composite of claim 2, wherein the epoxy resin has a Formula of

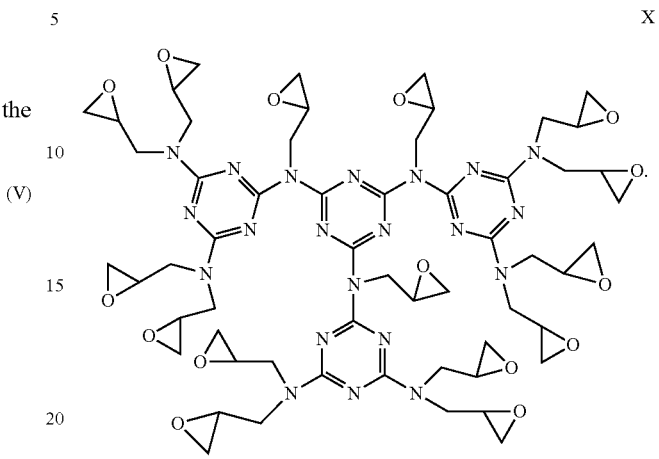
X

7. The carbon fiber composite of claim 2, wherein the epoxy resin has a Formula of

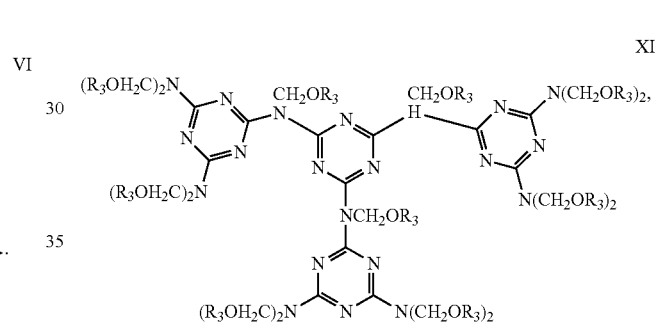
XI wherein $R_3$ is

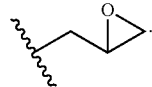

8. An isocyanate terminated, cross-linked polyurethane, polyester, or silicone, wherein the isocyanate terminated polyurethane, polyester, or silicone are cross-linked with a compound of Formula III

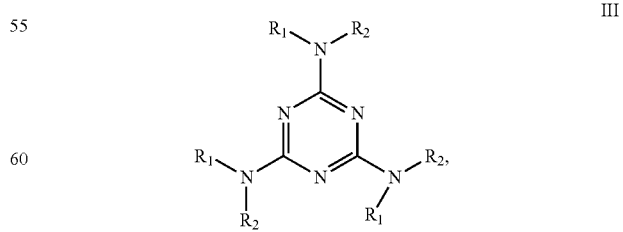
III wherein $R_1$ and $R_2$ are independently selected from the group consisting of $CH_2OH$ $CH_2NH_2$, and melaminyl, or are cross-linked with a compound having a formula of

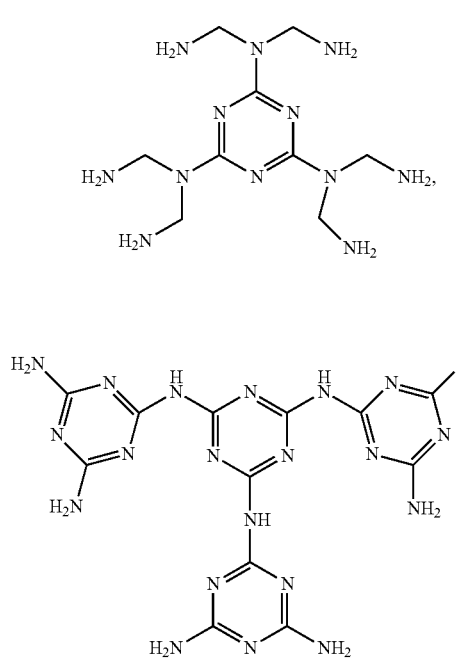

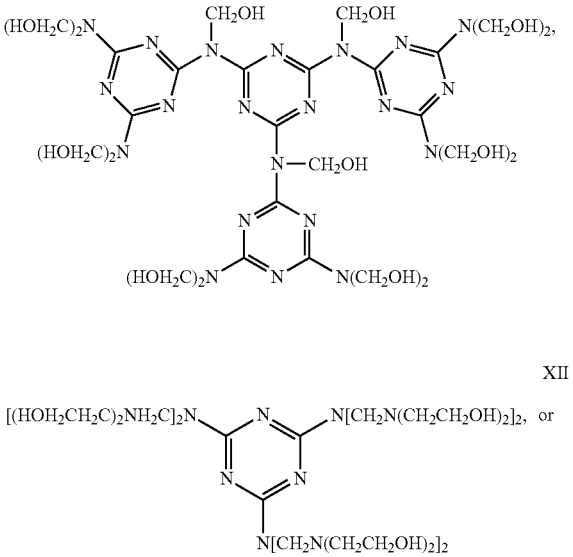

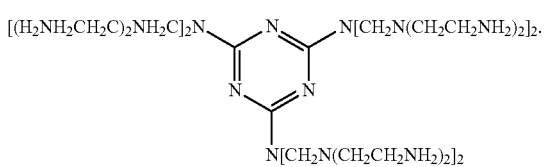

9. The isocyanate terminated, cross-linked polyurethane, polyester, or silicone of claim 8, wherein the isocyanate terminated polyurethane, polyester, or silicone are cross-linked with a compound of Formula III

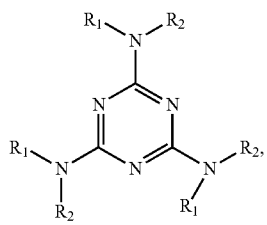

wherein $R_1$ and $R_2$ are independently selected from the group consisting of $CH_2OH$, $CH_2NH_2$, and melaminyl.

10. The isocyanate terminated, cross-linked polyurethane, polyester, or silicone of claim 9, wherein $R_1$ and $R_2$ are $CH_2OH$.

11. The isocyanate terminated, cross-linked polyurethane, polyester, or silicone of claim 9, wherein $R_1$ and $R_2$ are $CH_2NH_2$.

12. The isocyanate terminated, cross-linked polyurethane, polyester, or silicone of claim 9, wherein $R_1$ and $R_2$ are melaminyl.

13. The isocyanate terminated, cross-linked polyurethane, polyester, or silicone of claim 8, wherein the isocyanate terminated polyurethane, polyester, or silicone are cross-linked with a compound having a formula of:

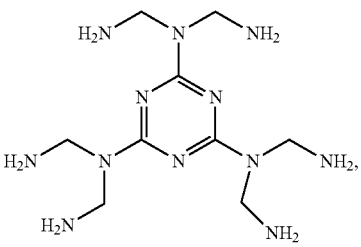

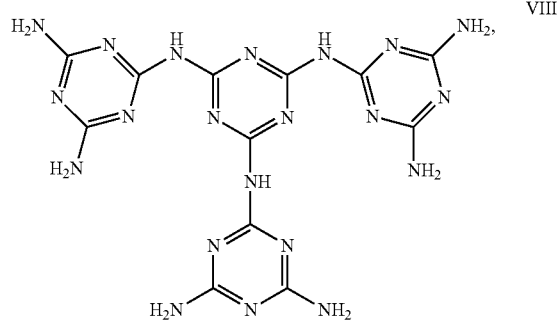

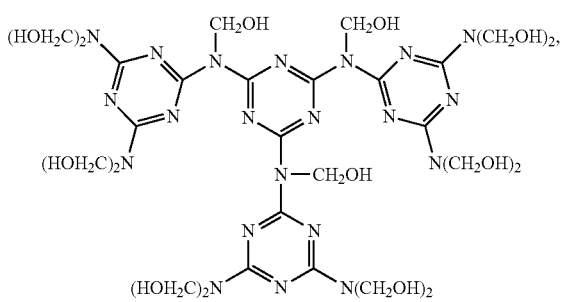

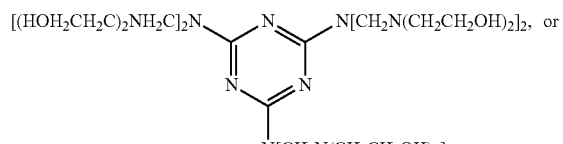

XII

XIII

14. The isocyanate terminated, cross-linked polyurethane, polyester, or silicone of claim 13, wherein the isocyanate terminated polyurethane, polyester, or silicone are cross-linked with a compound having a formula of

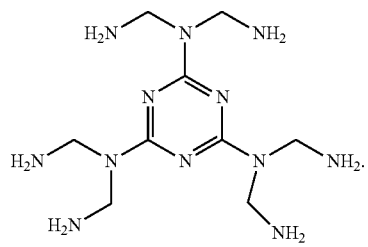

(IV)

15. The isocyanate terminated, cross-linked polyurethane, polyester, or silicone of claim 13, wherein the isocyanate terminated polyurethane, polyester, or silicone are cross-linked with a compound having a formula of

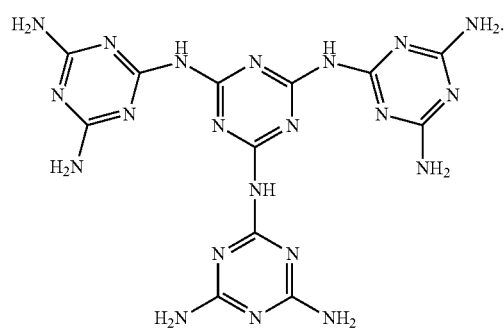

VIII

16. The isocyanate terminated, cross-linked polyurethane, polyester, or silicone of claim 13, wherein the isocyanate terminated polyurethane, polyester, or silicone are cross-linked with a compound having a formula of

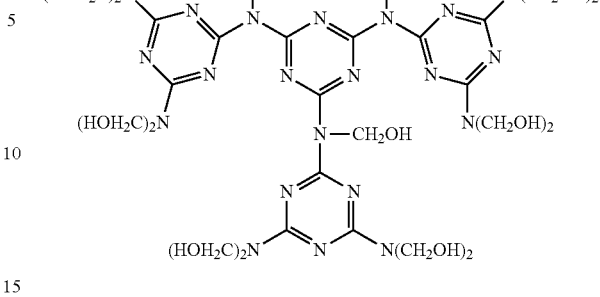

IX

17. The isocyanate terminated, cross-linked polyurethane, polyester, or silicone of claim 13, wherein the isocyanate terminated polyurethane, polyester, or silicone are cross-linked with a compound having a formula of

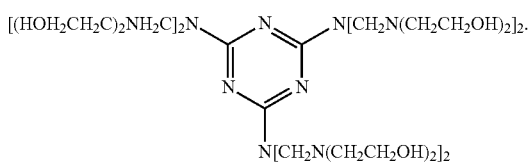

XII

18. The isocyanate terminated, cross-linked polyurethane, polyester, or silicone of claim 13, wherein the isocyanate terminated polyurethane, polyester, or silicone are cross-linked with a compound having a formula of

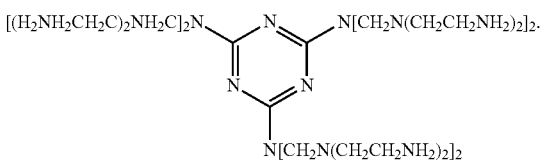

XIII

19. A method of making a compound of Formula IV, the method comprising contacting hexamethylol melamine with ammonia to produce a compound of Formula IV,

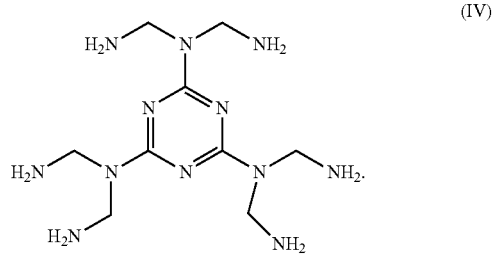 [SMILES: NCN(CN)c1nc(N(CN)CN)nc(N(CN)CN)n1]

(IV)

* * * * *

UNITED STATES PATENT AND TRADEMARK OFFICE
CERTIFICATE OF CORRECTION

PATENT NO. : 8,911,858 B2
APPLICATION NO. : 13/879289
DATED : December 16, 2014
INVENTOR(S) : Adam It is certified that error appears in the above-identified patent and that said Letters Patent is hereby corrected as shown below:

In the Specification

In Column 1, Line 33, delete "alliterative" and insert -- alterative --, therefor.

In Column 14, Line 21, delete "Lanthanium" and insert -- Lanthanum --, therefor.

In Column 16, Line 37, delete "formula XIII" and insert -- formula XIII. --, therefor.

In Column 23, Line 50, delete "R1" and insert -- $R_1$ --, therefor.

In Column 26, Line 16, delete "consisting of" and insert -- consisting of: --, therefor.

In Column 28, Line 14, delete "XIII" and insert -- XIII. --, therefor.

In Column 31, Lines 42-46, delete " 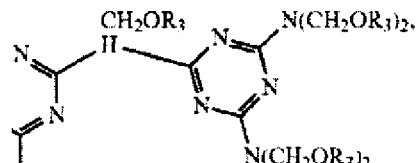 " and insert -- 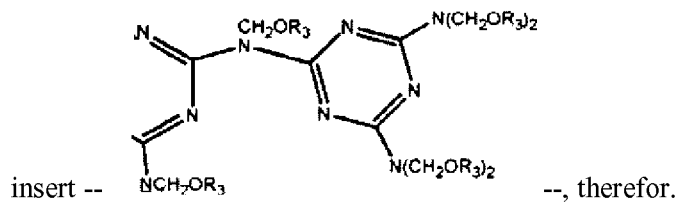 --, therefor.

In Column 34, Line 42, delete "cyanuryl" and insert -- cyanuric --, therefor.

In Column 36, Line 67, delete "Thermalstabilily" and insert -- Thermal stability --, therefor.

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,911,858 B2

In Column 37, Line 4, delete "forlmaline" and insert -- formalin --, therefor.

In Column 37, Line 19, delete "R1, R2 are NH2" and insert -- $R_1$, $R_2$ are $NH_2$ --, therefor.

In Column 37, Line 26, delete "N2," and insert -- $N_2$, --, therefor.

In Column 37, Line 49, delete "R1, R2" and insert -- $R_1$, $R_2$ --, therefor.

In Column 38, Line 14, delete "Pa s," and insert -- Pa.s, --, therefor.

In Column 38, Line 25, delete "Pa s." and insert -- Pa.s. --, therefor.

In Column 38, Line 37, delete "Pa s." and insert -- Pa.s. --, therefor.

In Column 38, Line 64, delete "Lanthaniumtrifluoro-methanesulphonate" and insert -- Lanthanumtrifluoro-methanesulphonate --, therefor.

In Column 40, Line 57, delete "aminocrosslinking" and insert -- amino crosslinking --, therefor.